US008420144B2

(12) United States Patent
Eto et al.

(10) Patent No.: US 8,420,144 B2
(45) Date of Patent: *Apr. 16, 2013

(54) KOKUMI-IMPARTING AGENT, METHOD OF USING, AND COMPOSITIONS CONTAINING SAME

(75) Inventors: Yuzuru Eto, Kawasaki (JP); Yusuke Amino, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 713 days.

This patent is subject to a terminal disclaimer.

(21) Appl. No.: 12/121,969

(22) Filed: May 16, 2008

(65) Prior Publication Data

US 2010/0136197 A1 Jun. 3, 2010

Related U.S. Application Data

(63) Continuation-in-part of application No. 12/117,027, filed on May 8, 2008, now Pat. No. 8,173,605, which is a continuation of application No. PCT/JP2006/322694, filed on Nov. 8, 2006.

(60) Provisional application No. 60/738,562, filed on Nov. 22, 2005, provisional application No. 60/807,831, filed on Jul. 20, 2006.

(30) Foreign Application Priority Data

Nov. 9, 2005 (JP) .................... 2005-325300
Jul. 7, 2006 (JP) .................... 2006-188458

(51) Int. Cl.
*A23L 1/228* (2006.01)

(52) U.S. Cl.
USPC ............ 426/535; 426/534; 530/331; 562/573

(58) Field of Classification Search .................. 426/534, 426/535; 530/331; 562/573
See application file for complete search history.

(56) References Cited

U.S. PATENT DOCUMENTS

| 3,331,828 | A | 7/1967 | Inamine et al. |
| 3,924,015 | A | 12/1975 | Winter et al. |
| 4,741,914 | A | 5/1988 | Kimizuke et al. |
| 4,758,551 | A | 7/1988 | Meister et al. |
| 4,927,808 | A | 5/1990 | Kitahara et al. |
| 5,089,476 | A | 2/1992 | Agouridas et al. |
| 5,409,904 | A | 4/1995 | Hecht et al. |
| 5,679,397 | A | 10/1997 | Kuroda et al. |
| 6,573,299 | B1 | 6/2003 | Petrus |
| 6,716,461 | B2 | 4/2004 | Miwa et al. |
| 6,733,797 | B1 | 5/2004 | Summers |
| 7,118,775 | B2 | 10/2006 | Kohmura et al. |
| 8,173,605 | B2 * | 5/2012 | Ohsu et al. ................. 514/21.91 |
| 2002/0061358 | A1 | 5/2002 | Miwa et al. |
| 2002/0176900 | A1 | 11/2002 | Yegorova |
| 2003/0211172 | A1 | 11/2003 | Jones et al. |
| 2004/0052920 | A1 | 3/2004 | Koike et al. |
| 2004/0116345 | A1 | 6/2004 | Besman et al. |
| 2004/0265471 | A1 | 12/2004 | Kohmura et al. |
| 2005/0244512 | A1 | 11/2005 | Holekamp et al. |
| 2006/0083847 | A1 | 4/2006 | Iwasaki et al. |
| 2006/0287390 | A1 | 12/2006 | Sagawa et al. |
| 2009/0130282 | A1 | 5/2009 | Hofmann et al. |
| 2009/0239310 | A1 | 9/2009 | Ohsu et al. |
| 2009/0239808 | A1 | 9/2009 | Ohsu et al. |
| 2009/0246835 | A1 | 10/2009 | Iwatani et al. |
| 2010/0105864 | A1 * | 4/2010 | Yoneda et al. ................. 530/331 |
| 2010/0120698 | A1 * | 5/2010 | Nagasaki et al. ............... 514/18 |
| 2010/0136197 | A1 | 6/2010 | Eto et al. |
| 2010/0183792 | A1 * | 7/2010 | Nagasaki et al. ............. 426/548 |
| 2011/0070270 | A1 * | 3/2011 | Kodera et al. ............. 424/278.1 |
| 2012/0034364 | A1 * | 2/2012 | Futaki et al. ................. 426/534 |

FOREIGN PATENT DOCUMENTS

| EP | 0449354 | 10/1991 |
| EP | 0 672 354 | 9/1995 |
| EP | 1197152 | 4/2002 |
| EP | 1 554 939 | 7/2005 |
| JP | 60-009465 | 1/1985 |
| JP | 60-232071 | 11/1985 |
| JP | 60-237963 | 11/1985 |
| JP | 7-188282 | 7/1995 |
| JP | 08-289760 | 11/1996 |
| JP | 10-276709 | 10/1998 |
| JP | 2002-138296 | 5/2002 |
| JP | 2002-369653 | 12/2002 |
| JP | 2004-215563 | 8/2004 |
| JP | 2004-267160 | 9/2004 |
| JP | 2005-046109 | 2/2005 |
| JP | 2006-158232 | 6/2006 |

(Continued)

OTHER PUBLICATIONS

Danner et al. Interaction of Glutathione Analogues with Hydra attenuata y-Glutamyltransferase. Biochemistry Journal. 1978. pp. 547-553.*
Copending U.S. Appl. No. 13/529,482.*
Copending U.S. Appl. No. 13/249,523.*
Copending U.S. Appl. No. 12/899,045.*
Copending U.S. Appl. No. 12/613,727.*
Copending U.S. Appl. No. 12/613,615.*
Copending U.S. Appl. No. 12/613,590.*
Final Report, "The quantification of natural occurring KF001 in food," pp. 1-8, Ajinomoto Co., Inc., Tokyo, Japan.
Breitweiser, G. E., et al., "Calcium sensing receptors as integrators of multiple metabolic signals," Cell Calcium 2004;35:209-216.
Brown, E. M., et al., "Cloning and characterization of an extracellular $Ca^{2+}$-sensing receptor from bovine parathyroid," Nature 1993;366:575-580.

(Continued)

*Primary Examiner* — Anthony Weier
(74) *Attorney, Agent, or Firm* — Shelly Guest Cermak; Cermak Nakajima LLP

(57) ABSTRACT

The present invention encompasses a method for screening for a kokumi-imparting substance by using the calcium receptor activity as an index, a composition containing a kokumi-imparting substance obtained by the screening method, a method for producing food or drink imparted with kokumi, and food or drink imparted with kokumi.

25 Claims, 4 Drawing Sheets

FOREIGN PATENT DOCUMENTS

| | | |
|---|---|---|
| JP | 2006-180792 | 7/2006 |
| JP | 2008-054507 | 3/2008 |
| WO | WO92/07267 | 4/1992 |
| WO | WO94/22438 | 10/1994 |
| WO | WO01/51629 | 7/2001 |
| WO | WO02/49653 | 6/2002 |
| WO | WO03/029417 | 4/2003 |
| WO | WO03/049687 | 6/2003 |
| WO | WO2007/042288 | 4/2007 |
| WO | WO2007/055388 | 5/2007 |
| WO | WO2007/055393 | 5/2007 |

OTHER PUBLICATIONS

McLarnon, S. J., et al., "Physiological and pharmacological agonists of the extracellular $Ca^{2+}$-sensing receptor," Eur. J. Pharmacol. 2002;447:271-278.

Morrot, G., et al., "The Color of Odors," Brain and Language 2001;79:309-320.

Squires, P. E., "Non-Ca2+-homeostatic functions of the extracellular $Ca^{2+}$-sensing receptor (CaR) in endocrine tissues," J. Endocrin. 2000;165:173-177.

Ueda, Y., et al., "Characteristic Flavor Constituents in Water Extract of Garlic," Agric. Biol. Chem. 1990;54(1):163-169.

Ueda, Y., et al., "Composition of Sulfur-Containing Components in Onion and Their Flavor Characters," Biosci. Biotech. Biochem. 1994;58(1):108-110.

International Search Report and Written Opinion of the International Searching Authority for PCT Patent App. No. PCT/JP2006/322694 (Mar. 16, 2007).

Shchukina, L.A., et al., "Synthesis and biological activity of glycolyl 3-glutathione," Inst. Khim. Prirod. Soed., Moscow, USSR, Zhurnal Obshchei Khimii (1967), 37(9), 1980-1987.

Cobb, M. H., et al., "Structural and Conformational Properties of Peptides Interacting with the Glutathione Receptor of Hydra," Mol. Pharmcol. 1982;21:629-636.

De Craecker, S., et al., "Characterization of the peptide substrate specificity of glutathionylspermidine synthetase from *Crithidia fasciculata*," Mol. Biochem. Parasitology 1997;84:25-32.

Leslie, E. M., et al., "Structural Reuirements for Functional Interaction of Glutathione Tripeptide Analogs with the Human Multidrug Resistance Protein 1 (MRP1)," J. Pharmacol. Experimental Therapeutics 2003;304(2):643-653.

Valyakina, T. I., et al., "Biological activity of peptide and depsipeptide analogs of ophthalmic [Y-glutamyl-α-aminobutyrylglycine] and norophthalmic [Y-glutamyl-alanylglycine] acids in glyoxalase I and formaldehyde: NAD-oxidoreductase enzyme systems," Biokhimiya 1972;37(4):757-761, with English abstract.

U.S. Appl. No. 12/117,027, filed May 8, 2008, Ohsu et al.

U.S. Appl. No. 12/117,041, filed May 8, 2008, Ohsu et al.

Kirimura, J., et al., "The Contribution of Peptides and Amino Acids to the Taste of Foodstuffs," J. Agric. Food Chem. 1969;17(4):689-695.

Jayyab, Nutritional Pharmacology of Glutathione, www.naturalhealthweb.com/articles/Jayyab.7.html, Self Improvement Online, Inc., 2003, pp. 1-2, retrieved Feb. 26, 2011.

English language translation of Valyakina, T. I., et al., "Study of the Biological Activity of Peptide and Depsipeptide Analogs of the Ophthalmic and Norophthalmic Acids in Glyoxalase I and Formaldehyde Enzyme Systems: Nad-Oxidoreductase," Biochem. 1972;37(4):757-760 (previously cited in the IDS of Sep. 28, 2009 with English abstract only).

Dunkel, A., et al., "Molecular and Sensory Characterization of γ-Glutamyl Peptides as Key Contributors to the Kokumi Taste of Edible Beans (*Phaseolus vulgaris* L.)," J. Agric. Food Chem. 2007;55:6712-6719.

Ueda, Y., et al., "Flavor Characteristics of Glutathione in Raw and Cooked Foodstuffs," Biosci. Biotech. Biochem. 1997;61(12):1977-1980.

International Search Report for PCT Patent App. No. PCT/JP2008/058325 (May 27, 2008).

International Preliminary Report on Patentability for PCT Patent App. No. PCT/JP2008/058325 (Dec. 3, 2009).

Suzuki, H., et al., "Improvement of the Flavor of Amino Acids and Peptides Using Bacterial γ-Glutamyltranspeptidase," Recents Highlight in Flavor Chemistry & Biology 2007, pp. 227-232, Eds. Hofmann, T., et al., Deutsche Forschungsanstalt für Lebensmittelchemie, Garching, Germany.

Supplementary European Search Report for EP Patent App. No. 08752255.3 (Oct. 27, 2010).

Notice of Reason for Rejection in Japanese Patent App. No. 2010-034162 (Jan. 25, 2011) with English translation thereof.

Office Action issued in U.S. Appl. No. 12/117,027 (Jan. 4, 2011).

Abdulrahim Jayyab, Nutritional Pharmacology of Glutathione, www.naturalhealthweb.com/article/Jayyab.7.html, Self Improvement Online, Inc. 2003, p. 1-2.

Ueda, Y. et al., "Glutathione in raw and Cooked Foodstuffs," Biosci. Biotech. Biochem. 1997;61(12):1977-1980.

Anonymous: "Calcium sensing receptor," Wikipedia (English language), Aug. 27, 2010, XP002598415, Retrieved from the Internet: URL: http://en.wikipedia.org/wiki/Calcium-sensing_receptor.

Bevilacqua, M., et al., "Increased Gastrin and Calcitonin Secretion after Oral Calcium or Peptones Administration in Patents with Hypercalciuria: A Clue to an Alteration in Calcium-Sensing Receptor Activity," J. Clin. Endocrinol. Metab. 2005;90(3):1489-1494.

Canaff, L., et al., "Extracellular Calcium-sensing Receptor Is Expressed in Rat Hepatocytes," J. Biol. Chem. 2001;276(6):4070-4079.

Chattopadhyay, N., et al., "Expression of Extracellular Calcium-Sensing Receptor by Human Lens Epithelial Cells," Biochem. Biophys. Res. Comm. 1997;233:801-805.

Chattopadhyay,, N., et al., "Mitogenic Action of Calcium-Sensing Receptor on Rat Calvarial Osteoblasts," Endocrinol. 2004;145(7):3451-3462.

Cheng, I., et al., "Identification and Localization of the Extracellular Calcium-Sensing Receptor in Human Breast," J. Clin. Endocrinol. Metab. 1998;83(2):703-707.

Cheng, S. X., et al., "Expression of calcium-sensing receptor in rat colonic epithelium: evidence for modulation of fluid secretion," Am. J. Physiol. Gastrointest. Liver Physiol. 2002;283:240-250.

Cifuentes, M., et al., "Calcium-Sensing Receptor Expression in Human Adipocytes," Endocrinology 2005;146(5):2176-2179.

Conigrave, A. D., et al., "L-Amino acid sensing by the calcium-sensing receptor: a general mechanism for coupling protein and calcium metabolism?" Eur. J. Clin. Nutr. 2002;56:1072-1080.

Conigrave, A. D., et al., "L-Amino acid sensing by the extracellular $Ca^{2+}$-sensing receptor," PNAS 2000;97(9):4814-4819.

Database CA [online], Chemical Abstracts Services, Columbus, OH, US; May 12, 1984, Valyakina, T. I., et al.; Biological activity of peptide and depsipeptide analogs of ophthalmic [.gamma.-glutamyl-.alpha.-aminobutyrylglycine] and norophthalmic [.gamma.-glutamyl-alanylglycine] acids in glyoxalase I and formaldehyde: NAD-oxidoreductase enzyme systems; XP-002438771, 1 pg.

House, M. G., et al., "Expression of an Extracellular Calcium-Sensing Receptor in Human and Mouse Bone Marrow Cells," J. Bone Min. Res. 1997;12(12):1959-1970.

Jensen, B., et al., "High extracellular calcium attenuates adipogenesis in 3T3-L1 preadipocytes," Exp. Cell Res. 2004;301:280-292.

Li, X., et al., "Net efflux of cysteine, glutathione and related metabolites from rat hippocampal slices during oxygen/glucose deprivation: dependence on γ-glutamyl transpeptidase," Brain Res. 1999;815:81-88.

Li, X., et al., "γ-Glutamyl Peptides and Related Amino Acids in Rat Hippocampus in vitro: Effect of Depolarization and γ-Glutamyl Transpeptidase Inhibition," Neurochem. Int. 1996;29(2):121-128.

Malaisse, W. J., et al., "Possible Participation of an Islet B-Cell Calcium-Sensing Receptor in Insulin Release," Endocrine 1999;11(3):293-300.

Nemeth, E. F., et al., "Calcimimetics with potent and selective activity on the parathyroid calcium receptor," Proc. Natl. Acad. Sci. USA 1998;95:4040-4045.

Olszak, I. T., et al., "Extracellular calcium elicits a chemokinetic response from monocytes in vitro and in vivo," J. Clin. Investigation 2000;105(9):1299-1299-1305.

Tu, Chia-Ling, et al., "The role of the calcium-sensing receptor in epidermal differentiation," Cell Calcium 2004;35:265-273.

Wang, M., et al., "Activation of Family C G-protein-coupled Receptors by the Tripeptide Glutathione," J. Biol. Chem. 2006;281(13):8864-8870.

Yamauchi, M., et al., "Involvement of calium-sensing receptor in osteoblastic differentiation of mouse MC3T3-E1 cells," Am. J. Physiol. Endocrinol. Metab. 2004;288:E608-E616.

International Search Report and Written Opinion of the International Searching Authority for PCT/JP2006/322684 (Jul. 13, 2007).

International Preliminary Report on Patentability for PCT Patent App. No. PCT/JP2006/322684 (May 22, 2008).

European Search Report for EP Patent App. No. 10002380.3 (Sep. 17. 2010).

Partial European Search Report for EP Patent App. No. 10012901.4 (Feb. 17, 2011).

Notice of Reason for Rejection for JP Patent App. No. 2010-034162 (Jan. 25, 2011).

The Notice of Reason for Rejection issued on Nov. 1, 2011 from the Japanese Patent Office in the corresponding Japanese Patent App. No. 2011-066637 with an English translation.

Goodman and Gilman's Manual of Pharmacology and Therapeutics, pp. 528-543 and 1059-1074 (Eds: Brunton & Parker; McGraw-Hill, 2008).

U.S. Appl. No. 12/861,929, filed Aug. 24, 2010, Hara et al.
U.S. Appl. No. 12/888,479, filed Sep. 23, 2010, Takeuchi et al.
U.S. Appl. No. 12/899,045, filed Oct. 6, 2010, Kodera et al.

* cited by examiner

KOKUMI-IMPARTING AGENT, METHOD OF USING, AND COMPOSITIONS CONTAINING SAME

This application claims priority under 35 U.S.C. §119 to Japanese Patent Application No. 2005-325300, filed on Nov. 9, 2005, U.S. Provisional Patent Application No. 60/738,562, filed on Nov. 22, 2005, Japanese Patent Application No. 2006-188458, filed on Jul. 7, 2006, and U.S. Provisional Patent Application No. 60/807,831, filed on Jul. 20, 2006, and is a continuation-in-part application under 35 U.S.C. §120 of U.S. patent application Ser. No. 12/117,027, filed on May 8, 2008 now U.S. Pat. No. 8,173,605, which is a continuation of PCT Patent Application No. PCT/JP2006/322694, filed on Nov. 8, 2006, the contents of which are incorporated by reference in their entireties. The Sequence Listing filed electronically herewith is also hereby incorporated by reference in its entirety (File Name: US-259CIP_Seq_List_Copy_1; File Size: 1 KB; Date Created: May 16, 2008).

BACKGROUND OF THE INVENTION

1. Field of the Invention

The present invention relates to a method of screening for a substance which imparts kokumi, a composition containing a substance which imparts kokumi obtained by the screening method, a method for producing a food, seasoning, or drink imparted with kokumi, and a food or drink imparted with kokumi.

2. Brief Description of the Related Art

The calcium receptor (also called the calcium sensing receptor, CaSR) contains 1078 amino acids, and is classified as in class C of the seven-transmembrane receptors (G protein-coupled receptor; GPCR). The cloning of the gene for the calcium receptor was reported in 1993 (Nature, 1993 Dec. 9; 366(6455):575-80). The calcium receptor is known to cause various cellular responses through elevation of the intracellular calcium levels, etc., when activated with calcium, etc. The sequence of the human calcium receptor gene is registered with GenBank (Accession No. NM_000388), and is well conserved among many animal species.

The calcium receptor may promote or suppress various biological functions. Therefore, therapeutic agents which act as activators or inhibitors of the calcium receptor are appropriately used in the treatment of neurological diseases, hepatic diseases, cardiovascular diseases, digestive system diseases, and other diseases, depending on the pathological conditions. For example, the calcium receptor is able to detect increased levels of blood calcium in the parathyroid, and suppress secretion of the parathyroid hormone (PTH) to correct the blood calcium level. Therefore, reduction of the blood calcium level is an expected effect of administration of a calcium receptor activator. It has been reported that when a calcium receptor activator is used to treat secondary hyperparathyroidism in a hemodialysis patient, the PTH level is reduced without the calcium and phosphorus levels increasing.

Since functional studies of the calcium receptor have been conducted primarily during calcium homeostasis, applications so far typically concern bone metabolic diseases in which calcium regulation is involved. However, through analysis of genetic expression, it is now known that the calcium receptor is widely distributed in living bodies in addition to the parathyroid and kidney tissues (J. Endocrinol., 2000 May, 165(2):173-7 and Eur. J. Pharmacol., 2002 Jul. 5, 447(2-3):271-8), and the possibility that the calcium receptor is involved in many various biological functions and the etiology of many diseases has been proposed. For example, the calcium receptor is thought to be involved in the function of the liver, heart, lung, alimentary canal, lymphocyte, and pancreas. It has been confirmed that the calcium receptor is expressed in a wide range of tissues by analyses based on RT-PCR using RNAs extracted from rat tissues. Therefore, the increased importance of activators and inhibitors of the calcium receptor in various applications is becoming recognized.

Moreover, cations such as gadolinium, basic peptides such as polyarginine, polyamines such as spermine, amino acids such as phenylalanine, and so forth have been reported to be calcium receptor activators (Cell Calcium., 2004 Mar., 35(3): 209-16).

Although many specific calcium receptor activators have been developed as described above, few of these compounds are native to living bodies, and those that are native have very low activities. Therefore, therapeutic agents containing these activators pose serious problems including side effects, permeability, and sufficient activity. For example, although it is known that amino acids act on calcium receptors, their use as calcium receptor activators is difficult due their very weak activity. Moreover, although macromolecules such as polyarginine have been reported to be an activator as described above, the activator function is based on their actions as polyvalent cations, which have irregular structures. That is, peptides having a specific structure are not known to be useful as a calcium receptor activator.

In the field of foodstuffs, substances having specific tastes have been used for many years. In particular, substances having the five basic tastes, namely, sweet, salty, sour, bitter, and umami (a delicious taste) have been widely used as seasonings. Substances which enhance these basic tastes have also been widely used. One taste that does not fall within these five basic tastes is "kokumi". Kokumi means a taste that is not one of the five basic tastes. Kokumi is a taste that not only enhances the five basic tastes but also enhances the marginal tastes of the basic tastes, such as thickness, growth (mouthfulness), continuity, and harmony. Several methods for imparting kokumi have been reported so far. Substances that have been reported to impart kokumi include glutathione (Japanese Patent No. 1464928), heated products of gelatin and tropomyosin (Japanese Patent Laid-open Publication (KOKAI) No. 10-276709), sulfone group-containing compounds (Japanese Patent Laid-open Publication (KOKAI) No. 8-289760), a peptide containing the Asn-His sequence (WO2004/096836), and so forth.

Although the development of various kokumi-imparting substances has been attempted as described above, and those that have been commercialized have been mainly extracts of natural products, there are presently very few examples of isolation of a pure kokumi component from an extract of natural product, such as glutathione and N-(4-methyl-5-oxo-1-imidazolin-2-yl)sarcosine.

Therefore, the development of highly effective, safe, and inexpensive kokumi-imparting substances is desired, and a convenient and highly sensitive method of screening for a kokumi-imparting substance is needed for that purpose.

SUMMARY OF THE INVENTION

An aspect of the present invention is to provide a convenient and highly sensitive method for screening for a kokumi-imparting substance, a highly effective, safe and inexpensive kokumi-imparting agent, compositions containing these substances or agents, a method for producing food, seasoning, or drink imparted with kokumi, and food, seasoning, or drink imparted with kokumi.

It has been found that low molecular weight peptides, including glutathione, are able to activate the calcium receptor. Moreover, since glutathione is known to be a kokumi-imparting substance, other low molecular weight peptides which are known to be activators of the calcium receptor were evaluated for their ability to impart kokumi, and it was found that the low molecular weight peptides imparted kokumi. The present invention was accomplished on the basis of these findings.

It is an aspect of the present invention to provide a method for screening for a kokumi-imparting substance comprising utilizing calcium receptor activity as an index.

It is a further aspect of the present invention to provide the method as described above, wherein the kokumi-imparting substance enhances a taste selected from the group consisting of salty, umami, sweet, and sour.

It is a further aspect of the present invention to provide the method as described above comprising a) reacting a calcium receptor and a test substance, b) detecting calcium receptor activity of the test substance, and c) measuring the kokumi-imparting effect of the test substance having calcium receptor activity.

It is a further aspect of the present invention to provide a composition comprising the kokumi-imparting substance obtained by the method as described above.

It is a further aspect of the present invention to provide the composition as described above comprising a substance selected from the group consisting of γ-Glu-X-Gly, wherein X is an amino acid or an amino acid derivative except for Cys, γ-Glu-Val-Y, wherein Y is an amino acid or an amino acid derivative, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-γ-Glu-Val, γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), and combinations thereof.

It is a further aspect of the present invention to provide the composition as described above, wherein X is selected from the group consisting of Cys(SNO), Cys(S-allyl), Gly, Cys(S-Me), Abu, Cle, Aib, Pen, tLeu and Ser, and Y is selected from the group consisting of Gly, Val, Glu, Lys, Phe, Ser, Pro, Arg, Asp, Met, Thr, His, Orn, Asn, Cys, and Gln.

It is a further aspect of the present invention to provide the composition as described above comprising a substance represented by γ-Glu-X—OCH(Z)CO$_2$H, wherein X is an amino acid or an amino acid derivative, and Z is H or CH$_3$.

It is a further aspect of the present invention to provide the composition as described above, which has the property of enhancing a taste selected from the group consisting of salty, umami, sweet, and sour.

It is a further aspect of the present invention to provide a food composition comprising the composition as described above, and a composition comprising at least one compound having calcium receptor activation activity.

It is a further aspect of the present invention to provide the food composition as described above, wherein the compound having calcium receptor activation activity is selected from the group consisting of calcium, protamine, polyarginine, spermine, polylysine, glutathione, cinacalcet, and combinations thereof.

It is a further aspect of the present invention to provide a method for producing a food or drink imparted with kokumi comprising adding one or more of the compositions as described above to a food or drink to a concentration of 1 mass ppb to 99.9 mass %.

It is a further aspect of the present invention to provide a method for producing food or drink imparted with kokumi comprising adding a seasoning comprising the composition as described above at a concentration of 1 mass ppb to 99.9 mass % to food or drink to a concentration of 0.01 to 10 mass %.

It is a further aspect of the present invention to provide a food or drink imparted with kokumi obtained by the method as described above.

It is a further aspect of the present invention to provide a composition containing 1 mass ppb to 99.9 mass % of γ-Glu-Val-Gly and 1 mass ppb to 99.9 mass % of a substance selected from the group consisting of calcium, protamine, polyarginine, spermine, polylysine, glutathione, and cinacalcet.

It is a further aspect of the present invention to provide a composition comprising 1 mass ppb to 99.9 mass % of a substance selected from the group consisting of glutathione, protamine, polylysine, GABA, salt forms thereof, and combinations thereof, and 1 mass ppb to 99.9 mass % of calcium or a salt form thereof.

It is a further aspect of the present invention to provide a compound selected from the group consisting of:
a) γ-Glu-X-Gly, wherein X is selected from the group consisting of Asn, Gln, His, Lys, Orn, and Arg, and
b) γ-Glu-Val-Y, wherein Y is selected from the group consisting of Leu, Ile, Ser, Thr, Met, Cys, Asp, Asn, Gln, Lys, Orn, Arg, Phe, Tyr, Pro, Hyp, Trp, His, and Abu.

It is a further aspect of the present invention to provide a compound represented by γ-Glu-X—OCH(Z)CO$_2$H, wherein X is an amino acid or an amino acid derivative, and Z is H or CH$_3$.

It is a further aspect of the present invention to provide a compound described above, wherein X is t-Leu or Abu.

It is a further aspect of the present invention to provide a compound represented by γ-Glu-t-Leu-Gly.

It is a further aspect of the present invention to provide a method of imparting kokumi to a composition comprising adding to the composition the kokumi-imparting substance obtained by the method described above.

It is a further aspect of the present invention to provide the method described above, wherein the kokumi-imparting substance is selected from the group consisting of γ-Glu-X-Gly, wherein X is an amino acid or an amino acid derivative except for Cys, γ-Glu-Val-Y, wherein Y is an amino acid or an amino acid derivative, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-γ-Glu-Val, γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), and combinations thereof.

It is a further aspect of the present invention to provide the method described above, wherein X is selected from the group consisting of Cys(SNO), Cys(S-allyl), Gly, Cys(S-Me), Abu, Cle, Aib, Pen, tLeu or Ser, and the Y is Gly, Val, Glu, Lys, Phe, Ser, Pro, Arg, Asp, Met, Thr, His, Orn, Asn, Cys, and Gln.

It is a further aspect of the present invention to provide the method described above, wherein the kokumi-imparting substance is γ-Glu-Val-Gly.

It is a further aspect of the present invention to provide the method described above, wherein the kokumi-imparting substance is represented by γ-Glu-X—OCH(Z)CO$_2$H, wherein X is an amino acid or an amino acid derivative, and Z is H or CH$_3$.

It is a further aspect of the present invention to provide a method for imparting kokumi to a food or drink comprising adding a composition obtained by the method as described above to the food or drink.

DESCRIPTION OF THE PREFERRED EMBODIMENTS

Figure 1:
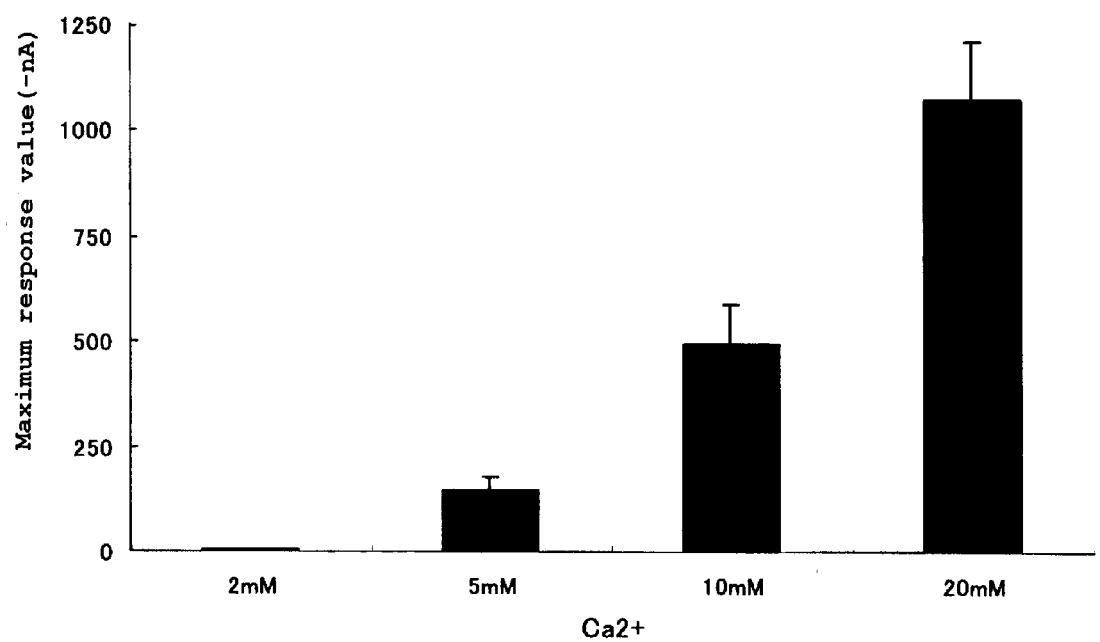
FIG. 1 shows the action of calcium on the calcium receptor by introducing the human calcium receptor cRNA into *Xenopus laevis* oocytes by microinjection. The intracellular response currents were recorded when a calcium chloride solution was added at an arbitrary concentration. The maximum intracellular currents were considered to be the response current values. No response was observed in control oocytes microinjected only with distilled water.

Provided is a convenient and highly sensitive method of screening for a kokumi-imparting substance, a highly effective, safe, and inexpensive composition containing the kokumi-imparting agent obtained by the screening method, a method for producing food, seasoning, or drink imparted with kokumi, and food, seasoning, or drink imparted with kokumi.

The calcium receptor can also be referred to as the calcium sensing receptor (CaSR), and belongs to class C of the seven-transmembrane receptors. The "calcium receptor activity" is when binding of a substrate to the calcium receptor activates the guanine nucleotide binding protein and, as a result, transmits one or more signals. Furthermore, the "calcium receptor activator" is a substance that acts on the calcium receptor to activate the calcium receptor and, as a result, controls the functions of cells expressing the calcium receptor.

"Kokumi" means a taste that is not one of the five basic tastes: sweet, salty, sour, bitter, and umami. Kokumi also means when a substance functions to enhance other properties of the five basic tastes, such as thickness, growth (mouthfulness), continuity, and harmony. Furthermore, a "kokumi-imparting agent" or "kokumi-imparting substance" refers to an agent or substance that can enhance one or more of the five basic tastes, and also enhance other properties of the basic tastes, such as thickness, growth (mouthfulness), continuity, and harmony which accompany the basic tastes. Therefore, the kokumi-imparting agent can also be used as a sweet taste-enhancing agent, salty taste-enhancing agent, sour taste-enhancing agent, bitter taste-enhancing agent, or umami-enhancing agent. As for the intensity of kokumi, the "first and middle taste" means the taste that is experienced from 0 to 4 seconds after eating, and the "aftertaste" means the taste that is experienced 5 seconds after eating.

All the amino acids and amino acid residues which make up the peptides are L-isomers, unless otherwise specified.

Method for Screening for Kokumi-Imparting Substance

The method for screening for a kokumi-imparting substance is characterized by using calcium receptor activity as an index. Specifically, this screening method includes steps of reacting a calcium receptor and a test substance, detecting calcium receptor activity of the test substance, and measuring the kokumi-imparting effect of the test substances having calcium receptor activation activity.

The specific process steps of the screening method are exemplified below. However, the steps of the screening method are not limited to these steps. The steps are as follows:

1) A test substance is added to a system which is set up to measure the calcium receptor activity of the test substance, and the calcium receptor activity is measured.

2) The calcium receptor activity of the test substance is compared to the same system in which no test substance is added (control), and these two values are compared.

3) The test substance having a higher calcium receptor-stimulating activity when the test substance is added is chosen.

4) The kokumi-imparting effect of the chosen test substance is measured, and a test substance having a kokumi-imparting effect is chosen.

The calcium receptor activity is measured by using, for example, a measurement system using cells expressing the calcium receptor. The cells may be cells endogenously expressing the calcium receptor, or recombinant cells which have been transformed with a foreign calcium receptor gene. As the aforementioned calcium receptor activity measurement system, any system may be used without particular limitation so long as the chosen system is able to detect when an extracellular ligand (activator) specific to the calcium receptor is added to the cells expressing the calcium receptor, and the activator binds (reacts with) to the calcium receptor, or a detectable signal is transmitted into the cells in response to binding (reaction) of the activator and the calcium receptor. When the reaction of the tested compound results in calcium receptor activity, this tested compound is determined to have calcium receptor activation activity and be a kokumi-imparting compound.

The kokumi-imparting effect can be confirmed by a taste test by a human, or the like. Furthermore, the test substance used in the screening method is not particularly limited, and may include low molecular weight compounds, saccharides, peptides, proteins, and so forth.

The human calcium receptor encoded by the human calcium receptor gene (GenBank Accession No. NM_000388) is preferred. However, the chosen calcium receptor is not limited to the protein encoded by the gene of the aforementioned reported GenBank sequence, but it may also be a protein encoded by a gene having a homology of 60% or more, preferably 80% or more, more preferably 90% or more, to the aforementioned sequence, so long as the protein functions as a calcium receptor. The GPRC6A receptor and the 5.24 receptor are also known to be subtypes of the calcium receptor, and they can also be used in the screening method described herein. The calcium receptor function can be examined by expressing a gene of interest in a cell and measuring changes in the electric current, or intracellular calcium ion concentration at the time of the addition of calcium.

The origin of the calcium receptor is not particularly limited, and examples include, besides the aforementioned human calcium receptor, calcium receptors derived from animals such as mouse, rat, and dog.

As described above, the calcium receptor activity can be confirmed by using live cells which express a calcium receptor or a fragment thereof, cell membranes which express a calcium receptor or a fragment thereof, an in vitro system containing a calcium receptor or a fragment thereof, or the like.

An example using live cells is shown below. However, confirmation of the calcium receptor activity is not limited to this example.

The calcium receptor can be expressed in cultured cells such as *Xenopus laevis* oocytes, hamster ovarian cells, and human fetal kidney cells. The calcium receptor can be expressed by cloning a calcium receptor gene in a plasmid that contains a foreign gene and introducing the plasmid or cRNA obtained by using the plasmid as a template. To detect the reaction, electrophysiological techniques, fluorescent indicator reagents that indicate elevation of intracellular calcium level, and so forth, can be used.

Expression of the calcium receptor is first confirmed based on the response to calcium or a specific activator. Oocytes can be used that have an intracellular current with calcium at a concentration of about 5 mM, or cultured cells can be used that showed fluorescence of the fluorescent indicator reagent with calcium at a concentration of about 5 mM. Calcium concentration dependency is determined by changing the calcium concentration. Then, a test substance such as a peptide is prepared to a concentration of about 1 μM to 1 mM, and added to the oocytes or cultured cells, and the calcium receptor activity of the test substance such as the aforementioned peptide is measured.

Kokumi-Imparting Agent

The compositions described herein include those containing a kokumi-imparting substance which can be obtained by the screening method. The kokumi-imparting substance is typically the active ingredient in the composition. The composition may contain, for example, one or more of the following substances: γ-Glu-X-Gly, wherein X represents an amino acid or amino acid derivative except for Cys, γ-Glu-Val-Y, wherein Y represents an amino acid or amino acid derivative, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-γ-Glu-Val, γ-Glu-Val-NH₂, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, and γ-Glu-Cys(S-Me).

The composition may contain one or more substances represented by the following formula:

γ-Glu-X—OCH(Z)CO₂H.

In the formula, X represents an amino acid or an amino acid derivative, and Z represents H (hydrogen atom) or CH₃ (methyl group). Specifically, γ-Glu-Val-GlyA, γ-Glu-t-Leu-GlyA, γ-Glu-Abu-GlyA, γ-Glu-Val-LacA, γ-Glu-t-Leu-LacA, γ-Glu-Abu-LacA, and the like, are preferable. GlyA represents glycolic acid, and LacA represents butyric acid. Butyric acid may have S-configuration or R-configuration, and preferably a S-configuration. These substances are represented by the following formulas.

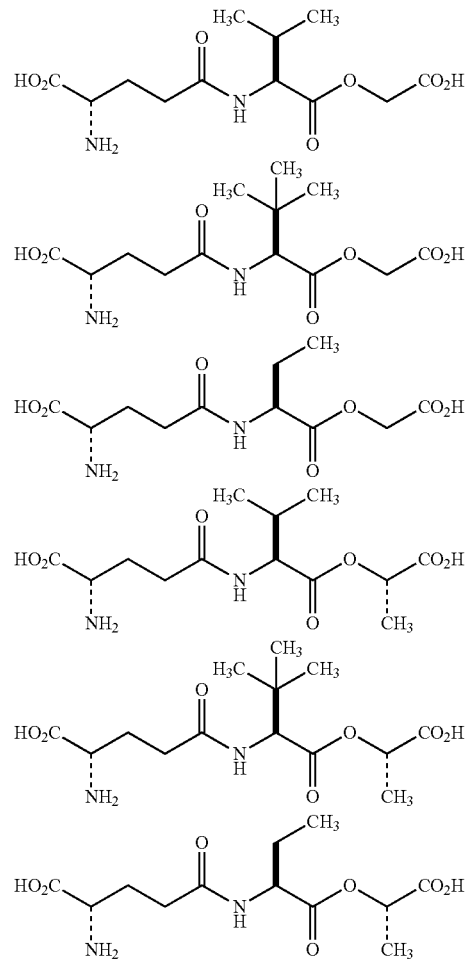

These substances may also be referred to as "peptides and amino acids used for the present invention". These peptides and amino acids can also be obtained by the screening method described above. Here, the term "peptide" includes both peptides and peptide derivatives, and the term "peptide derivative" means peptides composed of at least one amino acid derivative in the amino acid sequence. The term "amino acid" means, but is not limited to, neutral amino acids such as Gly, Ala, Val, Leu, Ile, Ser, Thr, Cys, Met, Asn, Gln, Pro, and Hyp, acidic amino acids such as Asp and Glu, basic amino acids such as Lys, Arg, and His, aromatic amino acids such as Phe, Tyr, Trp, and other amino acids such as Homoserine, Citrulline, Ornithine, alpha-Aminobutylic acid, Norvaline, Norleucine and Taurine. Also, the term "amino acid" may include a nonnatural amino acid (non-protein amino acid) such as tert-leucine, cycloleucine, α-aminoisobutyric acid, and L-penicillamine.

The abbreviations for the amino acid residues are as follows:
(1) Gly: Glycine
(2) Ala: Alanine
(3) Val: Valine
(4) Leu: Leucine
(5) Ile: Isoleucine
(6) Met: Methionine (7) Phe: Phenylalanine
(8) Tyr: Tyrosine
(9) Trp: Tryptophan
(10) His: Histidine
(11) Lys: Lysine
(12) Arg: Arginine
(13) Ser: Serine
(14) Thr: Threonine
(15) Asp: Aspartic acid
(16) Glu: Glutamic acid
(17) Asn: Aspargine
(18) Gln: Glutamine
(19) Cys: Cysteine
(20) Pro: Proline
(21) Orn: Ornithine
(22) Sar: Sarcosine
(23) Cit: Citruline
(24) N-Val: Norvaline
(25) N-Leu: Norleucine
(26) Abu: alpha-Aminobutylic acid
(27) Tau: Taurine
(28) Hyp: Hydroxyproline
(29) t-Leu: tert-leucine
(30) Cle: cycloleucine
(31) Aib: α-aminoisobutyric acid (2-methylalanin)
(32) Pen: L-penicillamine Furthermore, "amino acid derivative" means various types of derivatives of the above-mentioned amino acids, and may include, but are not limited to, unusual amino acids, nonnatural amino acids, amino alcohols, substituted amino acids wherein an amino acid side chain, such as carbonyl group, amino group, and/or thiol group, is substituted with various substituents. Such substituents include an alkyl group, acyl group, hydroxyl group, amino group, alkylamino group, nitro group, sulfonyl group, and various protection groups. Such substituted amino acids include, for example, Arg ($NO_2$): N-γ-nitro arginine, Cys (SNO): S-nitrocysteine, Cys (S-Me): S-methyl cysteine, Cys (S-allyl): S-allyl cysteine, Val-$NH_2$: valinamide, Val-ol: valinol (2-amino-3-methyl-1-butanol).

The "O" in the formulas γ-Glu-Met(O) and γ-Glu-Cys(S-Me)(O) indicates a sulfoxide structure. The "γ" in the formula γ-Glu indicates that glutamic acid bonds to another amino acid via the γ position of the carboxy group in the glutamic acid. γ-Glu-Cys(SNO)-Gly has the following structural formula:

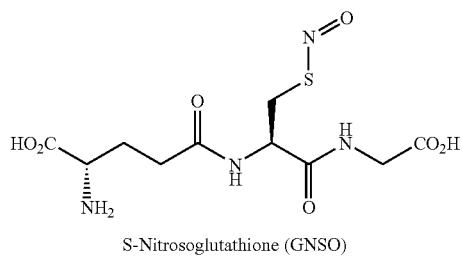 [SMILES: N[C@@H](CCC(=O)N[C@@H](CSN=O)C(=O)NCC(=O)O)C(=O)O]

S-Nitrosoglutathione (GNSO)

The following peptides have been found to impart kokumi and can be used in the compositions or the method of the present invention as described herein: γ-Glu-X-Gly, wherein the X represents an amino acid or amino acid derivative except for Cys, γ-Glu-Val-Y, wherein the Y represents an amino acid or amino acid derivative, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-γ-Glu-Val, γ-Glu-Val-$NH_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, and γ-Glu-Cys(S-Me).

Among these, compounds with the structural formula γ-Glu-X-Gly, wherein X represents Cys(SNO), Cys(S-allyl), Gly, Cys(S-Me), Abu, Cle, Aib, Pen, t-Leu or Ser, or γ-Glu-Val-Y, wherein Y represents Gly, Val, Glu, Lys, Phe, Ser, Pro, Arg, Asp, Met, Thr, His, Orn, Asn, Cys or Gln are preferred.

Also, the compounds represented by the formula γ-Glu-X—OCH(Z)$CO_2$H are newly synthesized novel substances and can be used in the present invention. Definitions of X and Z in the formula and preferable examples are the same as described above.

Among these, the following compounds are novel substances newly synthesized: γ-Glu-X-Gly, wherein X represents Asn, Gln, His, Lys, Orn, Cle, Aib, Pen, t-Leu or Arg, and γ-Glu-Val-Y, wherein Y represents Leu, Ile, Ser, Thr, Met, Cys, Asp, Asn, Gln, Lys, Orn, Arg, Phe, Tyr, Pro, Hyp, Trp, His, or Abu. Furthermore, among these novel substances, γ-Glu-X-Gly, wherein X represents Asn, Gln, His, Lys, Orn, Cle, Aib, Pen, t-Leu or Arg and γ-Glu-Val-Y, wherein Y represents Ser, Thr, Met, Cys, Asp, Asn, Gln, Lys, Orn, Arg, Pro or His are preferred.

These peptides and amino acids may be used alone, or in various combinations of two or more.

Although threshold concentrations, or the minimum concentrations which allow the sensing of taste, of known taste-imparting peptides are about 0.2% (1/10 of the threshold concentration of MSG), and thus their practicality is poor (J. Agr. Food Chem., vol. 23, No. 1, 49-53 (1975)), the compounds of the present invention show kokumi enhancing activity at an extremely low concentration of about 0.0001 to 0.1%, and thus they are extremely useful compounds due to their extremely high activity.

Commercially available peptides and amino acids, if available, can be used in the methods and compositions described herein. Furthermore, the peptides can be obtained by using a known technique such as chemical synthesis, or synthesis via an enzymatic reaction. Chemical synthesis is convenient since the number of amino acid residues of the peptides is small, for example, 2 or 3 residues. A peptide synthesizer can be used when chemically synthesizing the peptides, either entirely or partially. Examples of such methods include, for example, a peptide solid phase synthetic method. Peptides synthesized as described above can be purified by usual means, for example, ion exchange chromatography, reversed phase high performance liquid chromatography, affinity chromatography, and so forth. These peptide solid phase synthetic methods and the following peptide purification are well known in this technical field.

Furthermore, the peptides can also be prepared by an enzymatic reaction. For example, the method described in International Patent Publication WO2004/011653 can be used. That is, one amino acid or dipeptide with an esterified or amidated carboxyl terminus can be reacted with an amino acid having a free amino group, for example, an amino acid with a protected carboxyl group, in the presence of a peptide producing enzyme, and purifying the produced dipeptide or tripeptide. Examples of the peptide producing enzyme include a culture of microorganisms having an ability to produce peptides, microbial cells separated from such culture, processed products of these cells, peptide producing enzymes derived from such microorganisms, and so forth.

Salt forms of the peptides and amino acids are also included. Pharmacologically acceptable salts may be used for the salt forms of the peptides and amino acids. Examples of salts containing an acidic group such as a carboxyl group include ammonium salts, salts with alkali metals such as sodium and potassium, salt with alkaline earth metals such as calcium and magnesium, aluminum salts, zinc salts, salts with organic amines such as triethylamine, ethanolamine, morpholine, pyrrolidine, piperidine, piperazine, and dicyclohexylamine, and salts with basic amino acids such as arginine and lysine. Examples of salts with a basic group include salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzoic acid, pamoic acid, enanthoic acid, decanoic acid, teoclic acid, salicylic acid, lactic acid, oxalic acid, mandelic acid, and malic acid, and salts with organic sulfonic acids such as methanesulfonic acid, benzenesulfonic acid, and p-toluenesulfonic acid.

The method for using the kokumi-imparting substances obtained by the screening method described herein, and the compositions containing one or more of these substances is not particularly limited. For example, they can be added to food, seasonings, or drinks, either alone or in combination with other various additives, etc.

Furthermore, the kokumi-imparting agent may be employed alone, or in combination with other known compounds having kokumi-imparting activity, such as glutathione and alliin, or other various additives etc., which may be arbitrarily added. Moreover, the kokumi-imparting agent may contain one or more known compounds having calcium receptor activation activity.

Examples of these known compounds having calcium receptor activation activity include cations such as calcium and gadolinium cations, basic peptides such as polyarginine and polylysine, polyamines such as putrescine, spermine, and spermidine, proteins such as protamine, amino acids such as phenylalanine and glutathione, cinacalcet, and so forth. Salt forms of these compounds are also included. It has been found that glutathione has calcium receptor activation activity.

Also, it has been found that the kokumi-imparting activities of compounds having known kokumi-imparting activity, such as glutathione, as well as the kokumi-imparting agents described herein are also improved when formulated into a composition with compounds having calcium receptor activation activity.

Any known additives typically mixed with food, seasonings, or drink can be used without particular limitation. Examples of such additives include, for example, perfumes, saccharides, sweetners, dietary fibers, vitamins, amino acids such as sodium glutamate (MSG), nucleic acids such as inosine monophosphate (IMP), inorganic salts such as sodium chloride, water, and so forth.

The amount of the kokumi-imparting substance, agent, or composition which is obtained by the screening method described herein, may be employed in an amount effective for imparting kokumi, and can be suitably adjusted depending on the purpose. However, for seasoning, food, or drink, for example, it may be 1 mass ppb to 99.9 mass %, preferably 10 mass ppb to 99.9 mass %, more preferably 10 mass ppm to 10 mass % with respect to the seasoning, foodstuff, or drink, in terms of the total amount of the kokumi-imparting substance, agent, or composition.

Therefore, by adding one or more of the kokumi-imparting substances, agents, or compositions obtained by the screening method described herein, to food or drink so that the food or drink contains approximately 1 mass ppb to 99.9 mass %, preferably 10 mass ppb to 99.9 mass %, more preferably 10 mass ppm to 10 mass % of the substances or agents, food or drink imparted with kokumi can be produced.

Furthermore, food or drink imparted with kokumi can also be prepared by adding a seasoning containing 1 mass ppb to 99.9 mass % of one or more of the kokumi-imparting substances obtained by the screening method described herein. The kokumi-imparting agents, or compositions can be added to food or drink so that the food or drink contains 0.01 to 10 mass %, preferably 0.1 to 10 mass %, of the seasoning.

The kokumi-imparting substance obtained by the screening method described herein, or the compositions described herein may be in the form of a dry powder, paste, solution, or the like, and the physical properties thereof are not particularly limited.

EXAMPLES

Hereinafter, the present invention will be more specifically explained with reference to the following non-limiting examples.

Example 1

Preparation of Gene (cRNA)

The gene encoding the calcium receptor was prepared as follows. On the basis of the DNA sequence registered at NCBI (calcium receptor: NM_000388), synthetic oligo DNAs (forward primer (N) and reverse primer (C)) were prepared based on the DNA sequence registered at NCBI for the calcium receptor (NM_000388), and used for PCR (Table 1, SEQ ID NOS: 1 and 2).

TABLE 1

Synthetic oligo DNAs (forward primer (N) and reverse primer (C), h: human)

| Code | Sequence (5'-3') |
|---|---|
| hCASR_N | ACTAATACGACTCACTATAGGGACCATGGCATTTTATAGCTGCTGCTGG |
| hCASR_C | TTATGAATTCACTACGTTTTCTGTAACAG |

The primers shown in Table 1 (hCASR_N (SEQ ID NO: 1) and hCASR_C (SEQ ID NO: 2)) were synthesized from human kidney cDNA (Clontech), and PCR was performed with Pfu ultra DNA Polymerase (Stratagene) under the following conditions: after a reaction at 94° C. for 3 minutes, a cycle of reactions at 94° C. for 30 seconds, 55° C. for 30 seconds, and 72° C. for 2 minutes was repeated 35 times, and then a reaction was performed at 72° C. for 7 minutes. Whether amplification was attained by PCR was detected by agarose electrophoresis, staining with a DNA staining reagent, and ultraviolet irradiation. The length of the PCR products were confirmed by comparison with DNA markers of known sizes simultaneously subjected to electrophoresis. The plasmid vector pBR322 (Takara) was digested with the restriction enzyme EcoRV. The gene fragment amplified by PCR was ligated to the cleavage site of the plasmid by using Ligation Kit (Promega). The *Escherichia coli* DH5α strain was transformed with each ligation reaction solution, and the transformants containing the plasmid with the PCR amplification product were cloned was selected. The PCR amplification product was confirmed by DNA sequence analysis. By using this recombinant plasmid as a template together with a cRNA preparation kit (Ambion), the cRNA of the calcium receptor gene was prepared.

Example 2

Preparation of Various Samples 23 special grade amino acids were employed, including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, taurine (all of these from Ajinomoto), and hydroxyproline (Nakarai Tesque). Special grade amino acids were also used as D-Cys and D-Trp (Nakarai Tesque) and calcium chloride. Furthermore, the following peptide samples were used: γ-Glu-Cys-Gly (Sigma Aldrich Japan), γ-Glu-Cys(SNO)-Gly (Dojin Chemical Laboratory), γ-Glu-Ala (Bachem Feinchemikalien AG), γ-Glu-Gly (Bachem Feinchemikalien AG), γ-Glu-Cys (Sigma Aldrich Japan), γ-Glu-Met (Bachem Feinchemikalien AG), γ-Glu-Abu-Gly (Abu: α-aminobutyric acid, Bachem Feinchemikalien AG), γ-Glu-Thr (Kokusan Chemical), γ-Glu-Val (Kokusan Chemical), γ-Glu-Leu (contract manufactured product), γ-Glu-Ile (contract manufactured product), γ-Glu-Orn (Kokusan Chemical), Asp-Gly (contract manufactured product), Cys-Gly (contract manufactured product), Cys-Met (contract manufactured product), Glu-Cys (contract manufactured product), Gly-Cys (contract manufactured product), Leu-Asp (contract manufactured product), γ-Glu-Val-Val (contract manufactured product), γ-Glu-Val-Glu (contract manufactured product), γ-Glu-Val-Lys (contract manufactured product), γ-Glu-γ-Glu-Val (contract manufactured product), γ-Glu-Gly-Gly (contract manufactured product), γ-Glu-Val-Phe (contract manufactured product), γ-Glu-Val-Ser (contract manufactured product), γ-Glu-Val-Pro (contract manufactured product) γ-Glu-Val-Arg (contract manufactured product), γ-Glu-Val-Asp (contract manufactured product), γ-Glu-Val-Met (contract manufactured product), γ-Glu-Val-Thr (contract manufactured product), γ-Glu-Val-His (contract manufactured product), γ-Glu-Val-Asn (contract manufactured product), γ-Glu-Val-Gln (contract manufactured product), γ-Glu-Val-Cys (contract manufactured product), γ-Glu-Val-Orn (contract manufactured product), γ-Glu-Ser-Gly (contract manufactured product), and γ-Glu-Pen-Gly (contract manufactured product). Glutamine and cysteine were prepared upon use, and the other samples were stored at 20° C. after preparation. Peptides having a purity of 90% or higher were used, except for γ-Glu-Cys, which was at a purity of 80% or higher. The pH was adjusted, as needed, to an approximately neutral pH with NaOH or HCl. The solution used for dissolution of amino acids and peptides, preparation of *Xenopus laevis* oocytes, and culture of the oocytes had the following composition: 96 mM NaCl, 2 mM KCl, 1 mM $MgCl_2$, 1.8 mM $CaCl_2$, 5 mM Hepes, pH 7.2.

Example 3

Synthesis of γ-Glu-Val-Gly

Boc-Val-OH (8.69 g, 40.0 mmol) and Gly-OBzl•HCl (8.07 g, 40.0 mmol) were dissolved in methylene chloride (100 ml), and the solution was maintained at 0° C. Triethylamine (6.13 ml, 44.0 mmol), HOBt (1-hydroxybenzotriazole, 6.74 g, 44.0 mmol), and WSC•HCl (1-ethyl-3-(3-dimethylaminopropyl) carbodiimide hydrochloride, 8.44 g, 44.0 mmol) were added to the solution, and the mixture was stirred overnight at room temperature. The reaction mixture was concentrated under reduced pressure, and the residue was dissolved in ethyl acetate (200 ml). The solution was washed with water (50 ml), 5% citric acid aqueous solution (50 ml× twice), saturated brine (50 ml), 5% sodium hydrogencarbonate aqueous solution (50 ml× twice), and saturated brine (50 ml). The organic layer was dried over anhydrous magnesium sulfate, then the magnesium sulfate was removed by filtration, and the filtrate was concentrated under reduced pressure. The residue was recrystallized from ethyl acetate/n-hexane to obtain white crystals of Boc-Val-Gly-OBzl (13.2 g, 36.2 mmol).

Boc-Val-Gly-OBzl (5.47 g, 15.0 mmol) was added to 4 N HCl/dioxane solution (40 ml), and the mixture was stirred at room temperature for 50 minutes. Dioxane was removed by concentration under reduced pressure, n-hexane (30 ml) was added to the residue, and the mixture was concentrated under reduced pressure. This procedure was repeated 3 times to quantitatively obtain H-Val-Gly-OBzl•HCl.

Then, H-Val-Gly-OBzl•HCl and Z-Glu-OBzl (5.57 g, 15.0 mmol) were dissolved in methylene chloride (50 ml), and the solution was kept at 0° C. Triethylamine (2.30 ml, 16.5 mmol), HOBt (1-hydroxybenzotriazole, 2.53 g, 16.5 mmol), and WSC•HCl (1-ethyl-3-(3-dimethylaminopropyl) carbodiimide hydrochloride, 3.16 g, 16.5 mmol) were added to the solution, and the mixture was stirred at room temperature for 2 days. The reaction mixture was concentrated under reduced pressure, and the residue was dissolved in heated ethyl acetate (1500 ml). The solution was washed with water (200 ml), 5% citric acid aqueous solution (200 ml× twice), saturated brine (150 ml), 5% sodium hydrogencarbonate aqueous solution (200 ml× twice), and saturated brine (150 ml). The organic layer was dried over anhydrous magnesium sulfate, then the magnesium sulfate was removed by filtration, and the filtrate was concentrated under reduced pressure. The deposited crystals were collected by filtration, and dried under reduced pressure to obtain white crystals of Z-Glu(Val-Gly-OBzl)-OBzl (6.51 g, 10.5 mmol).

Then, Z-Glu(Val-Gly-OBzl)-OBzl (6.20 g, 10.03 mmol) was suspended in ethanol (200 ml), and 10% palladium/carbon (1.50 g) was added. A reduction reaction was performed at 55° C. for 5 hours under a hydrogen atmosphere. During the reaction, a total amount of 100 ml of water was gradually added. The catalyst was removed by filtration using a Kiriyama funnel, and the filtrate was concentrated under reduced pressure to a half volume. The reaction mixture was further filtered through a membrane filter, and the filtrate was concentrated under reduced pressure. The residue was dissolved in a small volume of water, ethanol was added to deposit crystals, and the crystals were collected by filtration and dried under reduced pressure to obtain a white powder of γ-Glu-Val-Gly (2.85 g, 9.40 mmol).

ESI-MS: $(M+H)^+$=304.1

$^1$H-NMR (400 MHz, $D_2O$) δ (ppm): 0.87 (3H, d, J=6.8 Hz), 0.88 (3H, d, J=6.8 Hz), 1.99-2.09 (3H, m), 2.38-2.51 (2H, m) 3.72 (1H, t, J=6.35 Hz), 3.86 (1H, d, J=17.8 Hz), 3.80 (1H, d, J=17.8 Hz), 4.07 (1H, d, J=6.8 Hz)

Example 4

Synthesis of γ-Glu-Cys(S-Me)-Gly [Cys(S-Me): S-methylcysteine]

Reduced glutathione (15.0 g, 48.8 mmol) was added to water (45 ml), and then sodium hydroxide (4.52 g, 2.2 equivalents, 107 mmol) was added little by little to the mixture while bubbled with nitrogen. Then, methyl iodide (4.56 ml, 1.5 equivalents, 73 mmol) was added to the mixture, and the mixture was sealed and stirred at room temperature for 2 hours. The reaction mixture was adjusted to pH 2 to 3 with concentrated hydrochloric acid, added with ethanol (150 ml), and stored overnight in a refrigerator. Since oily matter separated, the supernatant was removed. When the remaining oily matter was dissolved in water and ethanol was gradually added, partially crystallized oily matter was deposited. Therefore, the supernatant liquid was removed again. The residue was dissolved in water (300 ml), adsorbed onto an ion exchange resin (Dowex 1-acetate, 400 ml) applied to a column, and after washing with water, eluted with 1 N acetic acid aqueous solution. The eluate was concentrated under reduced pressure, and precipitated with water/ethanol to obtain a white powder of γ-Glu-Cys(S-Me)-Gly (5.08 g, 15.8 mmol).

FAB-MS: (M+H)$^+$=322

$^1$H-NMR (400 MHz, D$_2$O) δ (ppm): 2.14 (3H, s), 2.15-2.22 (2H, m), 2.50-2.58 (2H, m), 2.86 (1H, dd, J=9.0 Hz, J=14.0 Hz), 3.03 (1H, dd, J=5.0 Hz, J=14.0 Hz), 3.84 (1H, t, J=6.5 Hz), 3.99 (2H, S), 4.59 (1H, dd, J=5.0 Hz, J=9.0 Hz)

Example 5

Synthesis of Other Peptides

γ-Glu-Met(O), γ-Glu-Val-NH$_2$, γ-Glu-Val-ol, γ-Glu-Ser, γ-Glu-Tau, γ-Glu-Cys(S-Me)(O), γ-Glu-t-Leu, γ-Glu-Cys(S-allyl)-Gly, γ-Glu-Cys(S-Me), γ-Glu-Cle-Gly, and γ-Glu-Aib-Gly were synthesized in a manner similar to that described in Examples 3 and 4.

Example 6

Synthesis of γ-Glu-t-Leu-Gly

Boc-t-Leu-OH (9.26 g, 40.0 mmol) and Gly-OBzl•HCl (8.06 g, 40.0 mmol) were dissolved in methylene chloride (60 ml), and the solution was maintained at 0° C. Triethylamine (5.60 ml, 40.0 mmol), HOBt (1-hydroxybenzotriazole, 6.75 g, 44.0 mmol), and WSC•HCl (1-ethyl-3-(3-dimethylaminopropyl) carbodiimide hydrochloride, 8.47 g, 44.0 mmol) were added to the solution, and the mixture was stirred overnight at room temperature. The reaction mixture was concentrated under reduced pressure, and the residue was dissolved in ethyl acetate (200 ml). The solution was washed with water (50 ml), 5% citric acid aqueous solution (50 ml, twice), saturated brine (50 ml), 5% sodium hydrogencarbonate aqueous solution (50 ml, twice), and saturated brine (50 ml). The organic layer was dried over anhydrous magnesium sulfate, then the magnesium sulfate was removed by filtration, and the filtrate was concentrated under reduced pressure. The residue was recrystallized from ethyl acetate-n-hexane to obtain a viscous oily material of Boc-t-Leu-Gly-OBzl (15.20 g, 40.1 mmol).

Boc-t-Leu-Gly-OBzl (15.20 g, 40.1 mmol) was added to 4N—HCl/dioxane solution (200 ml), and the mixture was stirred at room temperature for an hour. Dioxane was removed by concentration under reduced pressure, n-hexane (30 ml) was added to the residue, and the mixture was concentrated under reduced pressure. This procedure was repeated 3 times to quantitatively obtain H-t-Leu-Gly-OBzl•HCl.

Then, H-t-Leu-Gly-OBzl•HCl and Z-Glu-OBzl (14.93 g, 40.2 mmol) were dissolved in methylene chloride (80 ml), and the solution was kept at 0° C. Triethylamine (5.60 ml, 40.2 mmol), HOBt (6.79 g, 44.2 mmol), and WSC•HCl (8.48 g, 44.2 mmol) were added to the solution, and the mixture was stirred at room temperature for 2 days. The reaction mixture was concentrated under reduced pressure, and the residue was dissolved in heated ethyl acetate (300 ml). The solution was washed with water (100 ml), 5% citric acid aqueous solution (100 ml twice), saturated brine (100 ml), 5% sodium hydrogencarbonate aqueous solution (100 ml twice), and saturated brine (100 ml). The organic layer was dried over anhydrous magnesium sulfate, then the magnesium sulfate was removed by filtration, and the filtrate was concentrated under reduced pressure. The residue was purified using silica-gel chromatography to obtain a viscous oily material of Z-Glu (t-Leu-Gly-OBzl)-OBzl (16.10 g, 25.5 mmol).

Then, Z-Glu(t-Leu-Gly-OBzl)-OBzl (16.10 g, 25.5 mmol) was suspended in ethanol (300 ml), and 10% palladium carbon (2.00 g) was added. A reduction was performed at room temperature for 5 hours under a hydrogen atmosphere. During the reaction, a total of 100 ml of water was gradually added. The catalyst was removed by filtration using a Kiriyama funnel (manufactured by Kiriyama glass Co.), and the filtrate was concentrated under reduced pressure to a half volume. The reaction mixture was further filtered through a membrane filter, and the filtrate was concentrated under reduced pressure. The residue was dissolved in a small volume of water, ethanol was added to deposit crystals, and the crystals were collected by filtration and freeze-dried to obtain a white powder of γ-Glu-t-Leu-Gly (6.70 g, 21.1 mmol).

ESI-MS: (M+H)$^+$=318.10.

$^1$H-NMR (400 MHz, D$_2$O) δ(ppm): 0.95 (9H, s), 2.04-2.08 (2H, m), 2.45-2.48 (2H, m), 3.73 (1H, t), 3.87-3.90 (2H, m), 4.07 (1H, s).

Example 7

Synthesis of γ-Glu-Abu-GlyA

Boc-Abu-OH (6.10 g, 30.0 mmol) and benzyl glycolate (H-GlyA-OBzl, 4.39 g, 30.0 mmol) were dissolved in methylene chloride (40 ml), and the solution was maintained at 0° C. DMAP (4-dimethylaminopyridine, 1.10 g, 9.0 mmol), and WSC•HCl (6.33 g, 33.0 mmol) were added to the solution, and the mixture was stirred overnight at room temperature. The reaction mixture was concentrated under reduced pressure, and the residue was dissolved in ethyl acetate (150 ml). The solution was washed with water (50 ml), 5% citric acid aqueous solution (50 ml twice), saturated brine (50 ml), 5% sodium hydrogencarbonate aqueous solution (50 ml twice), and saturated brine (50 ml). The organic layer was dried over anhydrous magnesium sulfate, then the magnesium sulfate was removed by filtration, and the filtrate was concentrated under reduced pressure to obtain a viscous oily material of Boc-Abu-GlyA-OBzl (9.47 g, 28.1 mmol).

The residue was added to 4N—HCl/dioxane solution (141 ml), and the mixture was stirred at room temperature for an hour. Dioxane was removed by concentration under reduced pressure, n-hexane (30 ml) was added to the residue, and the mixture was concentrated under reduced pressure. This procedure was repeated 3 times to quantitatively obtain H-Abu-GlyA-OBzl•HCl.

Then, H-Abu-GlyA-OBzl•HCl and Z-Glu-OBzl (10.47 g, 28.1 mmol) were dissolved in methylene chloride (100 ml), and the solution was kept at 0° C. Triethylamine (4.30 ml, 30.9 mmol), HOBt (4.74 g, 30.9 mmol), and WSC•HCl (5.95 g, 30.9 mmol) were added to the solution, and the mixture was stirred at room temperature for 2 days. The reaction mixture was concentrated under reduced pressure, and the residue was dissolved in heated ethyl acetate (200 ml). The solution was washed with water (50 ml), 5% citric acid aqueous solution (150 ml× twice), saturated brine (50 ml), 5% sodium hydrogencarbonate aqueous solution (50 ml× twice), and saturated brine (50 ml). The organic layer was dried over anhydrous magnesium sulfate, then the magnesium sulfate was removed by filtration, and the filtrate was concentrated under reduced pressure. The residue was purified using silica-gel chromatography to obtain a viscous oily material of Z-Glu (Abu-GlyA-OBzl)-OBzl (11.20 g, 19.0 mmol).

Then, Z-Glu(Abu-GlyA-OBzl)-OBzl (11.20 g, 19.0 mmol) was suspended in ethanol (150 ml), and 10% palladium carbon (2.00 g) was added. A reduction was performed at room temperature for 5 hours under a hydrogen atmosphere. During the reaction, a total amount of 50 ml of water was gradually added. The catalyst was removed by filtration using a Kiriyama funnel (manufactured by Kiriyama glass Co), and the filtrate was concentrated under reduced pressure to a half volume. The reaction mixture was further filtered through a membrane filter, and the filtrate was concentrated under reduced pressure. The residue was dissolved in water, and freeze-dried to obtain a white powder of γ-Glu-Abu-GlyA (5.00 g, 17.2 mmol).

ESI-MS: $(M+H)^+=291.10$.
$^1$H-NMR (400 MHz, $D_2O$) δ(ppm): 0.86 (3H, t, J=7.40 Hz), 1.60-1.74 (1H, m), 1.82-1.88 (1H, m), 2.04-2.12 (2H, m), 2.45 (2H, t, J=7.40 Hz), 3.79 (1H, t, J=6.36 Hz), 4.31-4.45 (1H, m), 4.57 (2H, s).

Example 8

Synthesis of γ-Glu-Val-GlyA

A white powder of γ-Glu-Val-GlyA was obtained at a yield of 77.5% in a manner similar to that described in Example 7, except that Boc-Val-OH was used instead of Boc-Abu-OH.

ESI-MS: $(M-H)^-=303.20$.
$^1$H-NMR (400 MHz, $D_2O$) δ(ppm): 0.90 (6H, t, J=6.52 Hz), 2.05-2.15 (2H, m), 2.15-2.25 (1H, m), 2.45-2.50 (2H, m), 3.80 (1H, t, J=6.52 Hz), 4.36 (1H, t, J=5.64 Hz), 4.61 (2H, s).

Example 9

Synthesis of γ-Glu-t-Leu-GlyA

A white powder of γ-Glu-t-Leu-GlyA was obtained at a yield of 73.4% in a manner similar to that described in Example 7, except that Boc-t-Leu-OH was used instead of Boc-Abu-OH.

ESI-MS: $(M+H)^+=319.20$.
$^1$H-NMR (400 MHz, $D_2O$) δ(ppm): 0.94 (9H, s), 2.03-2.10 (2H, m), 2.45-2.50 (2H, m), 3.78 (1H, t), 4.26 (1H, s), 4.60 (2H, s).

Example 10

Synthesis of γ-Glu-Abu-LacA

A white powder of γ-Glu-Abu-LacA was obtained at yield of 99.0% in a manner similar to that described in Example 7, except that benzyl(S)-Lactate(H-LacA-OBzl) was used instead of benzyl glycolate (H-GlyA-OBzl).

ESI-MS: $(M+H)^+=305.10$.
$^1$H-NMR (400 MHz, $D_2O$) δ(ppm): 0.91 (3H, t, J=7.40 Hz), 1.40 (3H, d, J=7.08 Hz), 1.60-1.75 (1H, m), 1.80-1.90 (1H, m), 2.00-2.12 (2H, m), 2.40-2.45 (2H, m), 3.74-3.78 (1H, m), 4.25-4.29 (1H, m), 4.89-4.95 (1H, m).

Example 11

Synthesis of γ-Glu-Val-LacA

A white powder of γ-Glu-Val-LacA was obtained at a yield of 78.0% in a manner similar to that described in Example 7, except that Boc-Val-OH was used instead of Boc-Abu-OH, and benzyl(S)-lactate(H-LacA-OBzl) was used instead of benzyl glycolate (H-GlyA-OBzl).

ESI-MS: $(M+H)^+=319.20$.
$^1$H-NMR (400 MHz, $D_2O$) δ(ppm): 0.85-0.92 (6H, m), 1.42 (3H, d, J=7.08 Hz), 2.02-2.11 (3H, m), 2.18-2.25 (1H, m), 2.42-2.50 (2H, m), 3.78 (1H, t, J=6.36 Hz), 4.20-4.31 (1H, m), 4.91-4.97 (1H, m).

Example 12

Synthesis of γ-Glu-t-Leu-LacA

A white powder of γ-Glu-t-Leu-LacA was obtained at a yield of 55.0% in a manner similar to that described in Example 7, except that Boc-t-Leu-OH was used instead of Boc-Abu-OH, and benzyl(S)-lactate(H-LacA-OBzl) was used instead of benzyl glycolate (H-GlyA-OBzl).

ESI-MS: $(M+H)^+=333.20$.
$^1$H-NMR (400 MHz, $D_2O$) δ(ppm): 0.96 (9H, s), 1.42 (3H, d, J=7.08 Hz), 2.05-2.10 (2H, m), 2.40-2.50 (2H, m), 3.73-3.78 (1H, m), 4.19 (1H, s), 4.90-5.00 (1H, m).

Example 13

Evaluation of Calcium Receptor Activation Activity

To evaluate calcium receptor activation activity, a Ca ion concentration-dependent Cl ionic current measuring method using a *Xenopus laevis* oocyte expression system was used. If each activator is added to *Xenopus laevis* oocytes expressing the calcium receptor, intracellular Ca ions increase. Then, the Ca ion concentration-dependent Cl channel opens, and the intracellular current value changes as an ionic current. By measuring the change in this intracellular current value, the presence or absence of calcium receptor activation activity can be determined.

Specifically, the abdomen of *Xenopus laevis* was opened, and an egg batch was taken out and treated with a 1% collagenase solution at 20° C. for 2 hours to obtain individual oocytes. Into the oocytes, 50 nl of 1 µg/µl receptor cRNA or 50 nl of sterilized water per oocyte was introduced by using a micro glass capillary, and the oocytes were cultured at 18° C. for 2 or 3 days. For the culture, a solution obtained by adding 2 mM pyruvic acid, 10 U/ml of penicillin, and 10 µg/ml of streptomycin to the solution in Example 2 was used. After the culture, a test solution was added to the oocytes containing either the cRNA or sterilized water. Electrophysiological measurement was performed by using an amplifier, Geneclamp500 (Axon), and recording software, AxoScope 9.0 (Axon). The oocytes were voltage-clamped at −70 mV by the double electrode voltage clamp method, and the intracellular current was measured via the Ca ion concentration-dependent Cl ion channel. The maximum value of the intracellular current was considered as the response current value.

Example 14

Evaluation of Calcium Receptor Activation Activity of Calcium

The calcium receptor activation activity of calcium was evaluated by using the method described in Example 13. That is, oocytes containing either cRNA of the calcium receptor or sterilized water were prepared, and voltage-clamped at −70 mV by the double electrode voltage clamp method. To the voltage-clamped oocytes, calcium was added (2 mM, 5 mM, 10 mM, 20 mM), and Ca ion concentration-dependent Cl response current was measured. The results are shown in FIG. 1. From these results, it was confirmed that the cRNA of the calcium receptor was functionally expressed in the oocytes. Furthermore, since the oocytes containing water did not respond to even high concentration calcium, it was confirmed that the calcium receptor is not expressed in the oocytes.

Example 15

Evaluation of Calcium Receptor Activation Activity of L-Amino Acids

Figure 2:
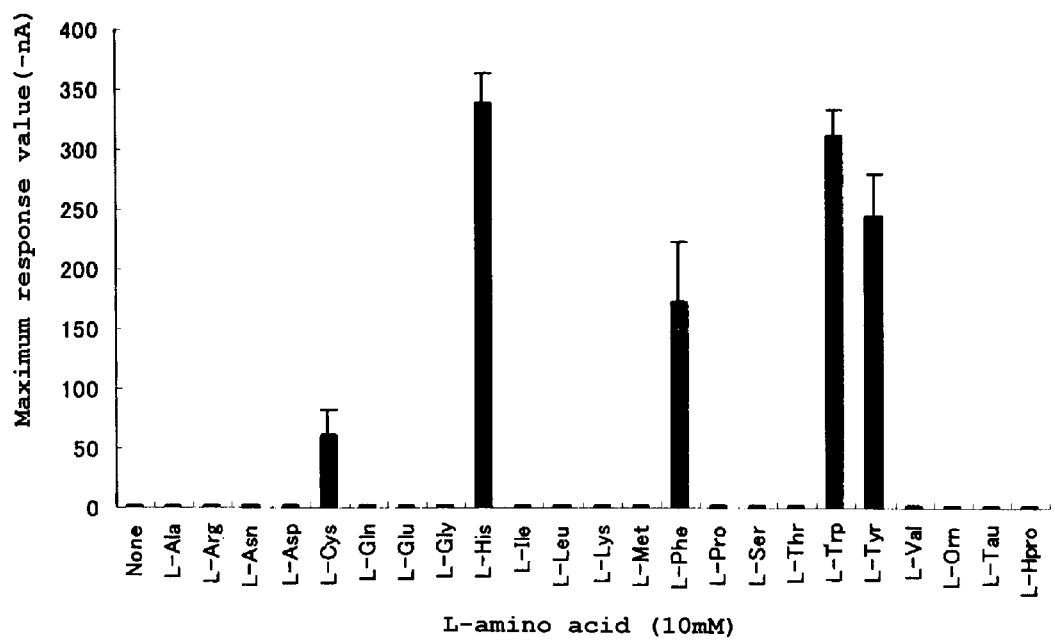
FIG. 2 shows the action of L-amino acids on the calcium receptor by introducing the human calcium receptor cRNA into *Xenopus laevis* oocytes by microinjection. The intracellular response currents were recorded when a 10 mM L-amino acid solution was added. The maximum intracellular currents were considered to be the response current values. No response was observed in control oocytes microinjected with only distilled water.

Calcium receptor activation activity of L-amino acids was evaluated by using the method described in Example 13. That is, oocytes containing either cRNA of the calcium receptor or sterilized water were prepared, and voltage-clamped at −70 mV by the double electrode voltage clamp method. To the voltage-clamped oocytes, alanine (10 mM), arginine (10 mM), asparagine (10 mM), aspartic acid (10 mM), cysteine (10 mM), glutamine (10 mM), glutamic acid (10 mM), glycine (10 mM), histidine (10 mM), isoleucine (10 mM), leucine (10 mM), lysine (10 mM), methionine (10 mM), phenylalanine (10 mM), proline (10 mM), serine (10 mM), threonine (10 mM), tryptophan (10 mM), tyrosine (10 mM), valine (10 mM), ornithine (10 mM), taurine (10 mM), or hydroxyproline (10 mM) was added, and Ca ion concentration-dependent Cl response current was measured. The results are shown in FIG. 2. By these results, it was demonstrated that cysteine, histidine, phenylalanine, tryptophan, and tyrosine had definite calcium receptor activation activity. As for the aforementioned amino acids, the activation activity was reported in Proc. Natl. Acad. Sci. USA, 2000 Apr. 25, 97(9):4814-9.

Example 16

Evaluation of Calcium Receptor Activation Activity of D-Cysteine

Figure 3:
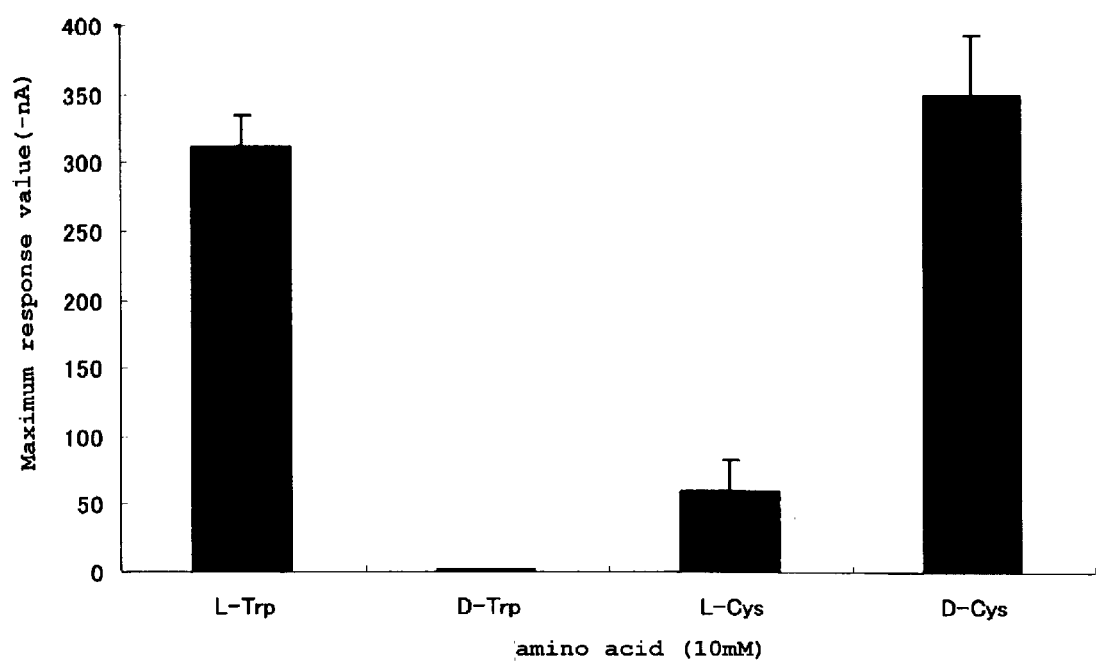
FIG. 3 shows the action of D-amino acids on the calcium receptor by introducing the human calcium receptor cRNA into *Xenopus laevis* oocytes by microinjection. The intracellular response currents were recorded when a 10 mM D-amino acid solution was added. The maximum intracellular currents were considered to be the response current values. No response was observed in control oocytes microinjected with only distilled water.

Calcium receptor activation activity of D-cysteine was evaluated by using the method described in Example 13. That is, oocytes containing either cRNA of the calcium receptor or sterilized water were prepared, and voltage-clamped at −70 mV by the double electrode voltage clamp method. To the voltage-clamped oocytes, D-cysteine (10 mM), L-cysteine (10 mM), D-tryptophan (10 mM), or L-tryptophan (10 mM) was added, and Ca ion concentration-dependent Cl response current was measured. The results are shown in FIG. 3. By these results, it was demonstrated that D-cysteine had definitive calcium receptor activation activity.

Example 17

Evaluation of Calcium Receptor Activation Activity of Peptides

Figure 4:
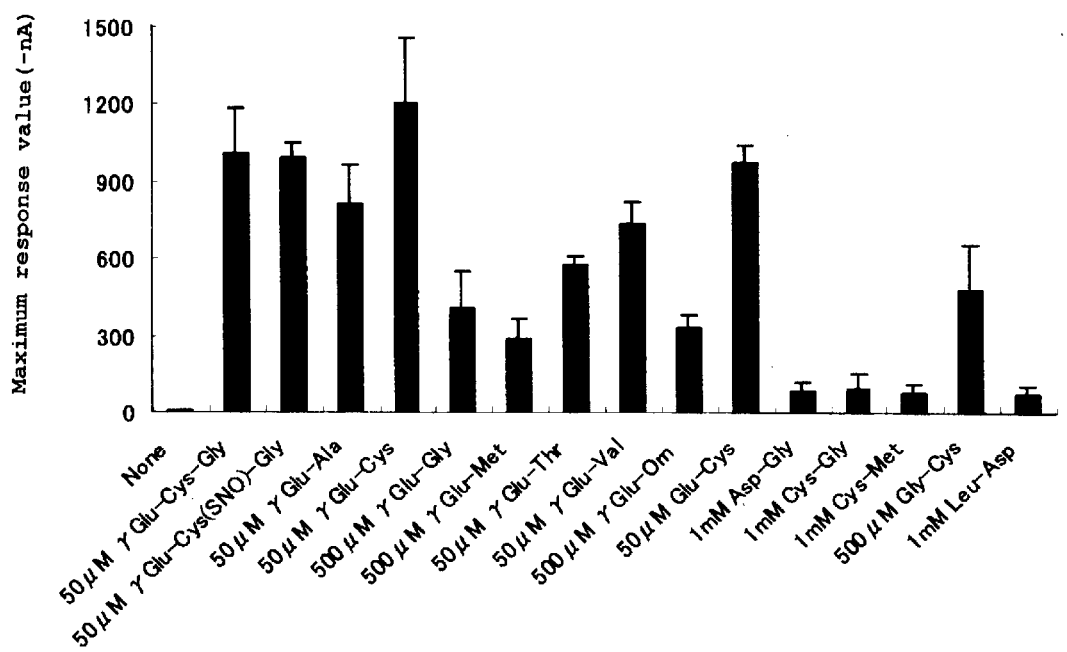
FIG. 4 shows the action of peptides on the calcium receptor by introducing the human calcium receptor cRNA into *Xenopus laevis* oocytes by microinjection. The intracellular response currents were recorded when a peptide solution was added at an arbitrary concentration. The maximum intracellular currents were considered to be the response current values. No response was observed in control oocytes microinjected with only distilled water.

Calcium receptor activation activity of peptides was evaluated by using the method described in Example 13. That is, oocytes containing either cRNA of the calcium receptor or sterilized water were prepared, and voltage-clamped at −70 mV by the double electrode voltage clamp method. To the voltage-clamped oocytes, γ-Glu-Cys-Gly (50 μM), γ-Glu-Cys(SNO)-Gly (50 μM), γ-Glu-Ala (50 μM), γ-Glu-Gly (500 μM), γ-Glu-Cys (50 μM), γ-Glu-Met (500 μM), γ-Glu-Thr (50 μM), γ-Glu-Val (50 μM), γ-Glu-Orn (500 μM), Asp-Gly (1 mM), Cys-Gly (1 mM), Cys-Met (1 mM), Glu-Cys (50 μM), Gly-Cys (500 μM), or Leu-Asp (1 mM) was added, and Ca ion concentration-dependent Cl response current was measured. The results are shown in FIG. 4. By these results, it was demonstrated that the aforementioned peptides had definitive calcium receptor activation activity.

Example 18

Evaluation of Calcium Receptor Activation Activity of Peptides

Calcium receptor activation activity of peptides was evaluated in the same manner as that of Example 17. Each of the peptides shown in Table 2 was added to voltage-clamped oocytes at 1000 μM, 300 μM, 100 μM, 30 μM, 10 μM, 3 μM, 1 μM, 0.3 μM, and 0.1 μM, and Ca ion concentration-dependent Cl response current was measured. The lowest concentration for which current was detected was shown in Table 2 as the activity. From these results, it became clear that these 32 peptides had calcium receptor activation activity.

TABLE 2

| No. | Peptide | Activity |
|---|---|---|
| 1 | γ-Glu-Met(O) | 1000 μM |
| 2 | γ-Glu-Val-Val | 1000 μM |
| 3 | γ-Glu-Val-Glu | 1000 μM |
| 4 | γ-Glu-Val-Lys | 1000 μM |
| 5 | γ-Glu-Val-Arg | 1000 μM |
| 6 | γ-Glu-Val-Asp | 1000 μM |
| 7 | γ-Glu-Val-Met | 1000 μM |
| 8 | γ-Glu-Val-Thr | 1000 μM |
| 9 | γ-Glu-γ-Glu-Val | 1000 μM |
| 10 | γ-Glu-Val-NH2 | 1000 μM |
| 11 | γ-Glu-Val-ol | 1000 μM |
| 12 | γ-Glu-Ser | 300 μM |
| 13 | γ-Glu-Tau | 300 μM |
| 14 | γ-Glu-Cys(S-Me)(O) | 300 μM |
| 15 | γ-Glu-Val-His | 100 μM |
| 16 | γ-Glu-Val-Orn | 100 μM |
| 17 | γ-Glu-Leu | 100 μM |
| 18 | γ-Glu-Ile | 100 μM |
| 19 | γ-Glu-t-Leu | 100 μM |
| 20 | γ-Glu-Cys(S-allyl)-Gly | 100 μM |
| 21 | γ-Glu-Val-Asn | 30 μM |
| 22 | γ-Glu-Gly-Gly | 30 μM |
| 23 | γ-Glu-Val-Phe | 30 μM |
| 24 | γ-Glu-Val-Ser | 30 μM |
| 25 | γ-Glu-Val-Pro | 30 μM |
| 26 | γ-Glu-Ser-Gly | 30 μM |
| 27 | γ-Glu-Cys(S-Me) | 30 μM |
| 28 | γ-Glu-Val-Cys | 10 μM |
| 29 | γ-Glu-Val-Gln | 10 μM |
| 30 | γ-Glu-Abu-Gly | 3 μM |
| 31 | γ-Glu-Cys(S-Me)-Gly | 3 μM |
| 32 | γ-Glu-Val-Gly | 0.1 μM |

Example 19

Evaluation of Calcium Receptor Activation Activity of Peptides

Calcium receptor (CaSR) activation activity of peptides obtained in Examples 2, 3, and 5-12 were measured as follows. A cDNA of human CaSR obtained in Example 1 of WO2007/055393A1 was inserted into an expression vector for an animal cell having a CMV promoter, and the cDNA in the vector was introduced into HEK 293 cells, which had multiplied to 70% of the maximal cell density, using FuGINE6 (Roche Ltd.). After culturing the cells for 4 to 48 hours, 0.6-1.0×10$^5$ of cells/well were disseminated into a 96-well plate, subsequently, the cells were cultured for one day, and then stained using Calcium 3 Assay Kit. The presence or absence of a calcium receptor activation activity of each peptide was confirmed by a calcium imaging method using FLEXSTATION (Molecular Devices Inc., instruction manual). Furthermore, the concentration of each peptide giving 50% of the maximal activity (EC50) was calculated using a dose characteristic curve.

TABLE 3

| compound | EC50, μM |
|---|---|
| γ-Glu-Val-Gly | 0.023-0.055 |
| γ-Glu-Cle-Gly | 0.5-1.5 |
| γ-Glu-Aib-Gly | 0.349-1.167 |
| γ-Glu-t-Leu-Gly | 0.043-0.077 |
| γ-Glu-Pen-Gly | 0.159-0.233 |
| γ-Glu-Val-GlyA | 0.14 |
| γ-Glu-t-Leu-GlyA | 0.05 |
| γ-Glu-Abu-GlyA | 0.065-0.079 |
| γ-Glu-Val-LacA | 0.057 |
| γ-Glu-t-Leu-LacA | 0.038 |
| γ-Glu-Abu-LacA | 0.102 |

* In Table 3, single numeric values represent n = 1, and the others represent n = 2 or 3.

Example 20

Kokumi-Imparting Activity of Peptides and Amino Acids

Calcium receptor activation activity was confirmed for the following peptides and amino acids: γ-Glu-X-Gly (X is Cys (SNO), Cys(S-allyl), Gly, Cys(S-Me), Abu, or Ser), γ-Glu-Val-Y (Y is Gly, Val, Glu, Lys, Phe, Ser, Pro, Arg, Asp, Met, Thr, His, Orn, Asn, Cys, or Gln), γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met(O), γ-Glu-γ-Glu-Val, γ-Glu-Val-NH₂, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, and γ-Glu-Cys(S-Me). Whether or not these peptides and amino acids have kokumi-imparting activity or not was determined by a sensory evaluation test, performed as follows. Samples of either alliin (S-allyl-cysteine sulfoxide: control for Kokumi-imparting activity), γ-Glu-Cys-Gly, γ-Glu-Cys, γ-Glu-Ala, or γ-Glu-Val were added to a final concentration of 0.2 g/dl to distilled water containing sodium glutamate (0.05 g/dl), inosine monophosphate (0.05 g/dl), and calcium chloride (1 mM) and kokumi-imparting activity was determined for each mixture. Sample solutions that became acidic after dissolution of the samples were adjusted to pH 6.8 to 7.2 with NaOH before use. The results are shown in Table 4.

TABLE 4

Kokumi-imparting activity of calcium receptor activators

| Calcium receptor activator | Kokumi-imparting activity |
|---|---|
| γ Glu-Cys-Gly | + |
| γ Glu-Cys | + |
| γ Glu-Ala | + |
| γ Glu-Val | + |

Example 21

Kokumi-Imparting Activity of Peptides

The intensity of the kokumi-imparting activity of each peptide having a confirmed calcium receptor activation activity was measured by a quantitative sensory evaluation test, performed as follows: Samples of either γ-Glu-Cys-Gly (glutathione), γ-Glu-Ala, γ-Glu-Met, or γ-Glu-Val were added to distilled water (0.1 g/dl) containing sodium glutamate (0.05 g/dl), inosine monophosphate (0.05 g/dl), and sodium chloride (0.5 g/dl), and the intensity of the kokumi-imparting activity was measured. Sample solutions that became acidic after dissolution of the samples were adjusted to pH 6.8 to 7.2 with NaOH before use. Sensory evaluation scores were used for evaluation based on the control sample (0 points) and the glutathione sample (3 points), and the test was performed with n=3. The results are shown in Table 5.

TABLE 5

| | | Intensity of kokumi | | |
|---|---|---|---|---|
| Sample | Concentration (g/dl) | First and middle taste | Aftertaste | Evaluation remarks |
| Control | — | 0 | 0 | — |
| γ-Glu-Cys-Gly | 0.1 | 3.0 | 3.0 | Thickness, growth (mouthfulness), and continuity were enhanced. |
| γ-Glu-Ala | 0.1 | 0.5 | 0.2 | Although the effect was weak, thickness was slightly enhanced. |
| γ-Glu-Met | 0.1 | 1.5 | 0.4 | Thickness, and growth (mouthfulness) were slightly enhanced. |
| γ-Glu-Val | 0.1 | 3.0 | 1.0 | Thickness, and growth (mouthfulness) were enhanced mainly for first and middle tastes |

Example 22

Kokumi-Imparting Activity of Peptides

The intensity of the kokumi-imparting activity of each peptide having confirmed calcium receptor activation activity was measured by a quantitative sensory evaluation test, performed as follows: Samples of either γ-Glu-Cys-Gly (glutathione), γ-Glu-Cys, γ-Glu-Val, or γ-Glu-Val-Gly were added to distilled water (0.1 g/dl, or 0.01 g/dl as required) containing sodium glutamate (0.05 g/dl), inosine monophosphate (0.05 g/dl), and sodium chloride (0.5 g/dl), was, and the intensity of the kokumi-imparting activity was measured. The sample solutions that became acidic after dissolution of the samples were adjusted to pH 6.8 to 7.2 with NaOH before use. Sensory evaluation scores were used for evaluation based on the control sample (0 points) and the glutathione sample (3 points), and the test was performed with n=5. The results are shown in Table 6.

TABLE 6

| Sample | Concentration (g/dl) | Intensity of kokumi First and middle taste | Aftertaste | Evaluation remarks |
|---|---|---|---|---|
| Control | — | 0 | 0 | — |
| γ-Glu-Cys-Gly | 0.1 | 3.0 | 3.0 | Thickness, growth (mouthfulness), and continuity were enhanced. |
| γ-Glu-Cys | 0.1 | 2.0 | 2.0 | The effect was slightly weaker, but substantially equivalent compared with γGlu-Cys-Gly |
| γ-Glu-Val | 0.1 | 3.0 | 1.0 | Thickness, and growth (mouthfulness) were enhanced mainly for first and middle tastes |
| γ-Glu-Val-Gly | 0.1 | * | * | * |
| γ-Glu-Val-Gly | 0.01 | 3.0 | 3.0 | Thickness, and continuity were mainly enhanced. Total taste was enhanced |

* Unmeasurable: Kokumi-imparting activity was too strong and could not be measured by the sensory evaluation.

Example 23

Kokumi-Imparting Activity of Peptides

The intensity of the kokumi-imparting activity of each peptide having confirmed calcium receptor activation activity was measured by a quantitative sensory evaluation test, performed as follows: Samples of either γ-Glu-Cys-Gly (glutathione), γ-Glu-Abu-Gly, or γ-Glu-Val-Gly were added to distilled water (0.1 g/dl or 0.01 g/dl) containing sodium glutamate (0.05 g/dl), inosine monophosphate (0.05 g/dl), and sodium chloride (0.5 g/dl), and the intensity of the kokumi-imparting activity was measured. Sample solutions that became acidic after dissolution of the samples were adjusted to pH 6.8 to 7.2 with NaOH before use. Sensory evaluation scores were used for evaluation based on the control sample (0 points) and the glutathione sample (3 points), and the test was performed with n=12. The results are shown in Table 7.

TABLE 7

| Sample | Concentration (g/dl) | Intensity of kokumi First and middle taste | Aftertaste | Evaluation remarks |
|---|---|---|---|---|
| Control | — | 0 | 0 | — |
| γGlu-Cys-Gly | 0.1 | 3.0 | 3.0 | Thickness, growth (mouthfulness), and continuity were enhanced. |
| γGlu-Abu-Gly | 0.01 | 3.0 | 2.0 | Thickness, and growth (mouthfulness) were enhanced mainly for first and middle tastes. |
| γGlu-Val-Gly | 0.01 | 3.0 | 3.0 | Thickness, and continuity were mainly enhanced. Total taste was enhanced. |

Example 24

Activity of Peptides on Basic Tastes

The intensity of the activity on basic tastes of each peptide having confirmed calcium receptor activation activity was measured by a quantitative sensory evaluation test, performed as follows: Samples of either γ-Glu-Cys-Gly (glutathione) or γ-Glu-Val-Gly were added to distilled water (0.0001 to 1 g/dl) containing sodium glutamate (0.2 g/dl) for the umami standard, sucrose (5 g/dl) for the sweet taste standard, sodium chloride (0.7 g/dl) or the salty taste standard, or citric acid (0.05 g/dl) for the sour taste standard, and the intensity of the activity on basic tastes was measured for each sample.

Sample solutions that became acidic after dissolution of the samples with respect to the standard solutions without the samples were adjusted with NaOH to pH not lower or higher by 0.2 than pH of the standard solutions before use. Sensory evaluation scores were used to evaluate the intensity as follows: 0 points for the control sample, 1 point for fairly intense activity as compared to the control, and 2 points for intense activity as compared to the control, and the test was performed with n=12. The samples showed that the basic tastes were enhanced at concentrations within the aforementioned broad concentration range. The results for typical concentrations are shown in Table 8.

TABLE 8

| Evaluation system | Distilled water | γGlu-Cys-Gly 0.10 g/dl | γGlu-Val-Gly 0.005 g/dl | γGlu-Val-Gly 0.01 g/dl |
|---|---|---|---|---|
| Umami | 0 | 0.7 | 0.7 | 1.5 |
| Sweet | 0 | 1.5 | 0.5 | 1.0 |

TABLE 8-continued

| Evaluation system | Distilled water | γGlu-Cys-Gly 0.10 g/dl | γGlu-Val-Gly 0.005 g/dl | γGlu-Val-Gly 0.01 g/dl |
|---|---|---|---|---|
| taste | | | | |
| Salty taste | 0 | 0.2 | 0.5 | 1.0 |
| Sour taste | 0 | 1.5 | 0.5 | 1.0 | sory evaluation scores were used for evaluation as follows: 0 points for the control sample, 3 points for intense activity as compared to the control, and 5 points for extremely intense activity as compared to the control, and the test was performed with n=12. The samples showed kokumi-imparting activity at concentrations within the aforementioned broad concentration range. The results for typical concentrations are shown in Table 9.

TABLE 9

| | | Intensity of kokumi | | |
|---|---|---|---|---|
| Sample | Concentration (g/dl) | First and middle taste | Aftertaste | Evaluation remarks |
| Control | — | 0 | 0 | — |
| γGlu-Cys-Gly | 0.01 | 3.0 | 3.0 | Thickness, growth (mouthfulness), and continuity were enhanced. |
| γGlu-Val-Gly | 0.0005 | 2.5 | 3.0 | Thickness and growth (mouthfulness) were mainly enhanced from first and middle taste. |
| γGlu-Val-Gly | 0.001 | 3.0 | 3.5 | Thickness and growth (mouthfulness) were mainly enhanced from first and middle taste. |
| γGlu-Val-Gly | 0.01 | 5.0 | 5.0 | Thickness and continuity were mainly enhanced. Total taste was enhanced. |
| γGlu-Val-Gly | 0.1 | 5.0 | 5.0 | Thickness and continuity were mainly enhanced. Total taste was enhanced. |

Example 25

Activity of Peptides for Imparting Kokumi to Consomme Soup

The intensity of activity for imparting kokumi to consomme soup of each peptide having confirmed calcium receptor activation activity was measured by a quantitative sensory evaluation test, performed as follows: Consomme soup was prepared by dissolving consomme soup powder (35% of sodium chloride, 18% of sodium glutamate, 0.2% of inosine monophosphate, 0.3% of white pepper powder, 0.5% of black pepper powder, 8.0% of beef extract powder, 3.0% of white wine powder, 2.0% of celery powder, 8.0% of Chinese cabbage extract powder, 2.5% of onion extract powder, 25.5% of lactose) at a concentration of 5 g/dl. To this consomme soup, samples of either γ-Glu-Cys-Gly (glutathione) or γ-Glu-Val-Gly was added to a concentration of 0.0001 to 1 g/dl, and the intensity of the kokumi-imparting activity was measured for each sample. The consomme soup with the samples that became acidic after dissolution of the samples with respect to the consomme soup without the samples was adjusted with NaOH to pH not lower or higher by 0.2 than pH of the consomme soup without the samples before use. Sen- Example 26

Activity of Peptides for Imparting Kokumi to Japanese Clear Soup

The intensity of activity for imparting kokumi to clear soup of each peptide having confirmed calcium receptor activation activity was measured by a quantitative sensory evaluation test, performed as follows: Japanese clear soup was prepared by adding 0.5 g/dl of soy sauce and 0.6 g/dl of sodium chloride to bonito kelp stock, obtained by adding 5 g of dried kelp to 3 L of water, heating the water, adding 25 g of dried bonito flakes just before boiling, and then filtering the water containing kelp and bonito flakes. To this clear soup, samples of either γ-Glu-Cys-Gly (glutathione) or γ-Glu-Val-Gly was added to a concentration of 0.0001 to 1 g/dl, and the intensity of the kokumi-imparting activity was measured for each sample. The clear soup with the samples that became acidic after dissolution of the samples with respect to the clear soup without the samples were adjusted with NaOH to pH not lower or higher by 0.2 than pH of the clear soup without the samples before use. Sensory evaluation scores were used to evaluate as follows: 0 points for the control sample, 3 points for intense activity as compared to the control, and 5 points for extremely intense activity as compared to the control, and the test was performed with n=12. The samples showed kokumi-imparting activity at concentrations within the aforementioned broad concentration range. The results for typical concentrations are shown in Table 10.

TABLE 10

| Sample | Concentration (g/dl) | Intensity of kokumi First and middle taste | Aftertaste | Evaluation remarks |
|---|---|---|---|---|
| Control | — | 0 | 0 | — |
| γGlu-Cys-Gly | 0.01 | 2.0 | 2.0 | Thickness and growth (mouthfulness) were enhanced. |
| γGlu-Val-Gly | 0.0005 | 2.5 | 3.0 | Thickness, growth (mouthfulness) and continuity were mainly enhanced from first and middle taste. |
| γGlu-Val-Gly | 0.001 | 3.5 | 4.0 | Thickness, growth (mouthfulness) and continuity were mainly enhanced from first and middle taste. |
| γGlu-Val-Gly | 0.01 | 5.0 | 5.0 | Thickness, and continuity were mainly enhanced. Total taste was enhanced. |
| γGlu-Val-Gly | 0.1 | 5.0 | 5.0 | Thickness, and continuity were mainly enhanced. Total taste was enhanced. |

Example 27

Activity of Peptides for Imparting Kokumi to Corn Soup

The intensity of the activity for imparting kokumi to corn soup of each peptide having confirmed calcium receptor activation activity was measured by a quantitative sensory evaluation test, performed as follows: to commercially available corn soup, samples of either γ-Glu-Cys-Gly (glutathione) or γ-Glu-Val-Gly were added to a concentration of 0.0001 to 1 g/dl, and the intensity of the kokumi-imparting activity was measured for each sample. The corn soup with the samples that became acidic after dissolution of the samples with respect to the corn soup without the samples was adjusted with NaOH to pH not lower or higher by 0.2 than pH of the corn soup without the samples before use. Sensory evaluation scores were used to evaluate as follows: 0 points for the control sample, 3 points for intense activity as compared to the control, and 5 points for extremely intense activity as compared to the control, and the test was performed with n=12. The samples showed kokumi-imparting activity at concentrations within the aforementioned broad concentration range. The results for typical concentrations are shown in Table 11.

TABLE 11

| Sample | Concentration (g/dl) | Intensity of kokumi First and middle taste | Aftertaste | Evaluation remarks |
|---|---|---|---|---|
| Control | — | 0 | 0 | — |
| γGlu-Cys-Gly | 0.01 | 3.0 | 3.0 | Richness, thickness and growth (mouthfulness) were enhanced. |
| γGlu-Val-Gly | 0.0005 | 2.5 | 3.0 | Sweet taste, growth (mouthfulness) and continuity were mainly enhanced from first and middle taste. |
| γGlu-Val-Gly | 0.001 | 3.5 | 4.0 | Sweet taste, growth (mouthfulness) and continuity were mainly enhanced from first and middle taste. |
| γGlu-Val-Gly | 0.01 | 4.5 | 5.0 | Growth (mouthfulness) and continuity were mainly enhanced. Total taste was enhanced. |
| γGlu-Val-Gly | 0.1 | 5.0 | 5.0 | Growth (mouthfulness) and continuity were mainly enhanced. Total taste was enhanced. |

Example 28

Activity of Peptides for Imparting Kokumi to Curry Sauce

The intensity of the activity for imparting kokumi to curry sauce of each peptide having confirmed calcium receptor activation activity was measured by a quantitative sensory evaluation test, performed as follows: to curry sauce prepared in a conventional manner by using commercially available curry roux, samples of either γ-Glu-Cys-Gly (glutathione) or γ-Glu-Val-Gly were added to a concentration of 0.0001 to 1 g/dl, and the intensity of kokumi-imparting activity was measured for each sample. The curry sauces with the samples that became acidic after dissolution of the samples with respect to the curry soup without the samples were adjusted with NaOH to pH not lower or higher by 0.2 than pH of the curry soup without the samples before use. Sensory evaluation scores were used to evaluate as follows: 0 points for the control sample, 3 points for intense activity as compared to the control, and 5 points for extremely intense activity as compared to the control, and the test was performed with n=12. The samples showed kokumi-imparting activity at concentrations within the aforementioned broad concentration range. The results for typical concentrations are shown in Table 12.

TABLE 12

| | | Intensity of kokumi | | |
|---|---|---|---|---|
| Sample | Concentration (g/dl) | First and middle taste | Aftertaste | Evaluation remarks |
| Control | — | 0 | 0 | — |
| γGlu-Cys-Gly | 0.01 | 3.0 | 3.0 | Richness, thickness and continuity were enhanced. |
| γGlu-Val-Gly | 0.001 | 2.5 | 3.0 | Mildness, richness and growth (mouthfulness) were mainly enhanced. |
| γGlu-Val-Gly | 0.005 | 3.5 | 4.0 | Mildness, richness and growth (mouthfulness) were mainly enhanced. |
| γGlu-Val-Gly | 0.01 | 5.0 | 5.0 | Richness and continuity were mainly enhanced. Total taste was enhanced. |
| γGlu-Val-Gly | 0.1 | 5.0 | 5.0 | Richness and continuity were mainly enhanced. Total taste was enhanced. |

Example 29

Kokumi-Imparting Activity Observed when Peptides and Additives Such as Known Calcium Receptor Activators were Used in Combination The intensity of the kokumi-imparting activity of each peptide having confirmed calcium receptor activation activity and a known calcium receptor activator used in combination was measured by a quantitative sensory evaluation test, performed as follows: Samples of γ-Glu-Cys-Gly (glutathione) or γ-Glu-Val-Gly (0.0001 to 1 g/dl), or these samples combined with a calcium receptor activator such as calcium lactate, protamine or polylysine, or GABA (addition concentration: 0.0001 to 1 g/dl) were added to distilled water containing sodium glutamate (0.05 g/dl), inosine monophosphate (0.05 g/dl), and sodium chloride (0.5 g/dl), and the intensity of the kokumi-imparting activity was measured. Sample solutions that became acidic after dissolution of the samples were adjusted to pH 6.8 to 7.2 with NaOH before use. Sensory evaluation scores were used to evaluate as follows: 0 points for the control sample, 3 points for intense activity (as intensity of 0.05 g/dl γ-Glu-Cys-Gly and 0.005 g/dl γ-Glu-Val-Gly), and 6 points for extremely intense activity (as twice intensity of 0.05 g/dl γ-Glu-Cys-Gly and 0.005 g/dl γ-Glu-Val-Gly), and the test was performed with n=12. The samples showed kokumi-imparting activity at concentrations within the aforementioned broad concentration range. The results for typical concentrations are shown in Table 13. As a result, a compound known to have kokumi-imparting activity, glutathione, can have improved kokumi-imparting activity when used with a known calcium receptor activator or the like such as calcium.

TABLE 13

| Peptide sample | Concentration (g/dl) | Additive | Concentration (g/dl) | Intensity of kokumi — First and middle taste | Aftertaste | Evaluation remarks |
|---|---|---|---|---|---|---|
| — | — | — | — | 0 | 0 | |
| γGlu-Cys-Gly | 0.05 | — | — | 3.0 | 3.0 | Thickness, growth (mouthfulness) and continuity |
| γGlu-Val-Gly | 0.005 | — | — | 3.0 | 3.0 | Thickness and continuity |
| — | — | Calcium lactate | 0.25 | 0.5 | 0.5 | Thickness |
| — | — | Protamine | 0.005 | 1.5 | 1.0 | Growth (mouthfulness) |
| — | — | Polylysine | 0.001 | 0.5 | 0.5 | Thickness |
| — | — | GABA | 0.025 | 0.5 | 0.5 | Thickness |
| γGlu-Cys-Gly | 0.05 | Calcium lactate | 0.25 | 3.5 | 4.0 | Thickness, growth (mouthfulness) and continuity |
| γGlu-Cys-Gly | 0.05 | Protamine | 0.005 | 4.5 | 4.5 | Thickness, growth (mouthfulness) and continuity |
| γGlu-Cys-Gly | 0.05 | Polylysine | 0.001 | 3.5 | 4.0 | Thickness, growth (mouthfulness) and continuity |
| γGlu-Cys-Gly | 0.05 | GABA | 0.025 | 4.5 | 4.5 | Thickness, growth (mouthfulness) and continuity |
| γGlu-Val-Gly | 0.005 | Calcium lactate | 0.25 | 5.0 | 5.0 | Thickness and continuity |
| γGlu-Val-Gly | 0.005 | Protamine | 0.005 | 4.5 | 4.5 | Thickness, growth (mouthfulness) and continuity |
| γGlu-Val-Gly | 0.005 | Polylysine | 0.001 | 4.5 | 4.5 | Thickness and continuity |
| γGlu-Val-Gly | 0.005 | GABA | 0.025 | 4.5 | 4.5 | Richness and thickness |

INDUSTRIAL APPLICABILITY

The specific amino acids and peptides having calcium receptor activation activity are also useful as kokumi-imparting substances. In particular, as shown in Examples 20 to 29, several kinds of dipeptides and tripeptides were newly discovered to be kokumi-imparting substances, and since they are peptides, they can be used in the field of foodstuffs in which high safety is demanded. In addition, since a method for screening for a kokumi-imparting substance utilizing calcium receptor activation as an index has been developed, so-called high throughput screening can be used, and thus development of a still more highly efficient kokumi substances is possible.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

The invention claimed is:

1. A compound represented by the formula: γ-Glu-X—OCH(Z)CO$_2$H, wherein X is an amino acid or an amino acid derivative, and Z is H or CH$_3$; and
X is not Ala or Cys when Z is H.

2. The compound according to claim 1, wherein X is t-Leu or Abu.

3. The compound according to claim 1, wherein said compound is a kokumi imparting substance.

4. A composition comprising the compound according to claim 3.

5. The composition according to claim 4, which is able to enhance a taste selected from the group consisting of salty, umami, sweet, and sour.

6. The composition according to claim 4, wherein said composition is a food or drink.

7. The composition according to claim 4, wherein said composition further comprises at least one other compound having calcium receptor activation activity.

8. The composition according to claim 7, wherein the other compound having calcium receptor activation activity is selected from the group consisting of calcium, protamine, polyarginine, spermine, polylysine, cinacalcet, and combinations thereof.

9. A method for producing a food or drink imparted with kokumi comprising adding one or more of the compositions according to claim 4 to a food or drink so that the concentration of said one or more compositions is 1 mass ppb to 99.9 mass %.

10. The method according to claim 9, wherein the composition is a seasoning and is present in the food or drink at a concentration of 0.01 to 10 mass %.

11. A method of imparting kokumi to a composition comprising adding to the composition a compound represented by the formula: γ-Glu-X—OCH(Z)CO$_2$H wherein X is an amino acid or an amino acid derivative, and Z is H or CH$_3$; and
X is not Ala or Cys when Z is H.

12. The method according to claim 11, wherein X is t-Leu or Abu.

13. The method according to claim 11, wherein said compound is a kokumi imparting substance.

14. A compound selected from the group consisting of γ-Glu-Val-GlyA, γ-Glu-t-Leu-GlyA, γ-Glu-Abu-GlyA, γ-Glu-Val-LacA, γ-Glu-t-Leu-LacA, and γ-Glu-Abu-LacA.

15. A compound represented by γ-Glu-Y-Gly, wherein Y is selected from the group consisting of Pen, and t-Leu.

16. The compound according to claim 15, wherein said compound is a kokumi imparting substance.

17. A composition comprising the compound according to claim 16.

18. The composition according to claim 17, which is able to enhance a taste selected from the group consisting of salty, umami, sweet, and sour.

19. The composition according to claim 17, wherein said composition is a food or drink.

20. The composition according to claim 17, wherein said composition further comprises at least one other compound having calcium receptor activation activity.

21. The composition according to claim 20, wherein the other compound having calcium receptor activation activity is selected from the group consisting of calcium, protamine, polyarginine, spermine, polylysine, cinacalcet, and combinations thereof.

22. A method for producing a food or drink imparted with kokumi comprising adding one or more of the compositions according to claim 17 to a food or drink so that the concentration of said one or more compositions is 1 mass ppb to 99.9 mass %.

23. The method according to claim 22, wherein the composition is a seasoning and is present in the food or drink at a concentration of 0.01 to 10 mass %.

24. A method of imparting kokumi to a composition comprising adding to the composition a compound represented by γ-Glu-Y-Gly, wherein Y is selected from the group consisting of Pen and t-Leu.

25. The method according to claim 24, wherein said compound is a kokumi imparting substance.

* * * * *

SEQUENCE LISTING

```
<160> NUMBER OF SEQ ID NOS: 2

<210> SEQ ID NO 1
<211> LENGTH: 49
<212> TYPE: DNA
<213> ORGANISM: Artificial
<220> FEATURE:
<223> OTHER INFORMATION: hCASR_N primer

<400> SEQUENCE: 1
actaatacga ctcactatag ggaccatggc attttatagc tgctgctgg            49

<210> SEQ ID NO 2
<211> LENGTH: 29
<212> TYPE: DNA
```

```
<213> ORGANISM: Artificial
<220> FEATURE:
<223> OTHER INFORMATION: hCASR_C primer

<400> SEQUENCE: 2
ttatgaattc actacgtttt ctgtaacag                                    29
```